(12) United States Patent
Kim et al.

(10) Patent No.: US 11,337,929 B2
(45) Date of Patent: May 24, 2022

(54) DRUG DELIVERY FORMULATION FOR TREATING MENTAL ILLNESS OR CENTRAL NERVOUS SYSTEM DISORDER

(71) Applicant: AJOU UNIVERSITY INDUSTRY-ACADEMIC COOPERATION FOUNDATION, Suwon-si (KR)

(72) Inventors: Moon Suk Kim, Suwon-si (KR); Ji Yeon Heo, Daegu (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 87 days.

(21) Appl. No.: 16/484,870

(22) PCT Filed: Feb. 8, 2018

(86) PCT No.: PCT/KR2018/001719
§ 371 (c)(1),
(2) Date: Aug. 9, 2019

(87) PCT Pub. No.: WO2018/147660
PCT Pub. Date: Aug. 16, 2018

(65) Prior Publication Data
US 2019/0374476 A1    Dec. 12, 2019

(30) Foreign Application Priority Data

Feb. 9, 2017  (KR) .................... 10-2017-0018235

(51) Int. Cl.
| | | |
|---|---|---|
| *A61K 31/496* | (2006.01) | |
| *A61K 9/50* | (2006.01) | |
| *A61K 9/00* | (2006.01) | |
| *A61K 45/06* | (2006.01) | |

(52) U.S. Cl.
CPC .......... *A61K 9/5031* (2013.01); *A61K 9/0019* (2013.01); *A61K 9/5026* (2013.01); *A61K 9/5042* (2013.01); *A61K 9/5089* (2013.01); *A61K 31/496* (2013.01); *A61K 45/06* (2013.01)

(58) Field of Classification Search
CPC .. A61K 9/5031; A61K 9/0019; A61K 9/5026; A61K 9/5042; A61K 9/5089; A61K 31/496; A61K 45/06
See application file for complete search history.

(56) References Cited

U.S. PATENT DOCUMENTS

| | | | |
|---|---|---|---|
| 8,940,311 B2 | 1/2015 | Lim et al. | |
| 2003/0176354 A1* | 9/2003 | Abajian | C07K 5/0812 |
| | | | 514/4.8 |
| 2006/0110458 A1* | 5/2006 | Hahn | C08B 37/0072 |
| | | | 424/488 |
| 2006/0188583 A1* | 8/2006 | Lim | A61P 19/02 |
| | | | 424/490 |
| 2008/0241267 A1 | 10/2008 | Verrijk | |
| 2014/0030350 A1 | 1/2014 | Ashrafi et al. | |
| 2014/0199244 A1 | 7/2014 | Rijcken et al. | |

FOREIGN PATENT DOCUMENTS

| | | | | |
|---|---|---|---|---|
| JP | 2008-517927 | A | 5/2008 | |
| JP | 2014-518264 | A | 7/2014 | |
| KR | 10-2007-0100701 | A | 10/2007 | |
| KR | 10-2010-0083118 | A | 7/2010 | |
| KR | 10-2014-0026364 | A | 3/2014 | |
| WO | WO-2014205126 | A1 * | 12/2014 | ........... C07C 13/263 |
| WO | 2016/040489 | A1 | 3/2016 | |
| WO | 2016/164578 | A1 | 10/2016 | |
| WO | 2017/015488 | A1 | 1/2017 | |

OTHER PUBLICATIONS

International Search Report for PCT/KR2018/001719 dated Jun. 7, 2018 (PCT/ISA/210).

* cited by examiner

*Primary Examiner* — Ali Soroush
(74) *Attorney, Agent, or Firm* — Sughrue Mion, PLLC

(57) ABSTRACT

A drug delivery formulation for treating a mental illness or a central nervous system disorder is disclosed. The drug delivery formulation includes a microcapsule containing a biodegradable polymer and a drug and a crosslinked hydrogel and a method for preparing the same. The drug delivery formulation can slowly release a drug at a constant rate without a burst of drug release in the early stage of drug administration to maintain a constant blood drug level over a long period of time and thus enjoys the advantage of preventing excessive initial release of drug, thereby obtaining a desirable sustained release profile by single administration without necessity for multiple administrations divided at regular time intervals.

7 Claims, 17 Drawing Sheets

Example 5-1

Example 5-2

Example 5-3

Example 5-4

APZ-cap + Cx-SIS          APZ-cap + Cx-HA

Example 10

Example 11

DRUG DELIVERY FORMULATION FOR TREATING MENTAL ILLNESS OR CENTRAL NERVOUS SYSTEM DISORDER

CROSS REFERENCE TO RELATED APPLICATIONS

This application is a National Stage of International Application No. PCT/KR2018/001719 filed Feb. 8, 2018, claiming priority based on Korean Patent Application No. 10-2017-0018235 filed Feb. 9, 2017.

TECHNICAL FIELD

The present invention relates to a drug delivery formulation for treating a mental illness or a central nervous system disorder and, more particularly, to a drug delivery formulation for treating a mental illness or a central nervous system disorder, comprising a microcapsule containing a biodegradable polymer and a drug and a crosslinked hydrogel and a method for preparing the same.

BACKGROUND ART

A mental illness or psychosis refers to a pathological condition that shows abnormalities in mental function, and thus one is unable to adapt to social life and disruptions in everyday life are caused, in a broad sense, but means the remaining morbid mental conditions in a narrow sense, except for a congenital mental disorder, that is, mental retardation or a psychopathy that causes deterioration in personality, or a psychogenic reaction (neurosis), and the like. This includes schizophrenia, schizophreniform disorder, schizoaffective disorder, bipolar disorder, non-bipolar mania, Tourette syndrome, cyclothymic disorder, rapid cycling, ultradian cycling, personality disorder, attention disorder that has or does not have hyperactivity, delusional disorder, brief psychotic disorder, shared psychotic disorder, psychotic disorder caused by a general medical condition, psychotic disorder related to Parkinson's disease, substance-induced psychotic disorder or unspecified psychotic disorder, anxiety disorder such as generalized anxiety disorder, panic disorder, post-traumatic stress disorder, impulse control disorder, phobic disorder and dissociative states.

Depression or depressive disorder is a type of mental illness, and refers to a disease that causes various cognitive, mental and physical symptoms, leading to a decline in daily functions, due to a decrease in motivation and a sense of depression as main syndromes. Since depression is caused by various causes and its symptoms are various, drugs that are used as antidepressants are administered for the purpose of alleviating or treating symptoms such as depression, manic depression, panic disorder, obsessive-compulsive disorder, eating disorders, other specific insomnia disorders, and chronic pain.

The nervous system is conveniently classified into the central nervous system (CNS) including the brain and the spinal cord and peripheral nerves consisting of ganglia, and among them, the central nervous system corresponds to a central processing unit which collects, integrates, and coordinates neural information. A central nervous system disorder collectively refers to a disease occurring in the brain or the spinal cord, and representative examples thereof include brain tumors (glioma), cerebral infarction, hypertensive intracerebral hemorrhage, cerebral contusion, cerebral arteriovenous malformation, brain abscesses, encephalitis, hydrocephalus, epilepsy, cerebral concussions, cerebral palsy, dementia, spinal cord tumors, spinal arteriovenous malformation, spinal cord infarction, and the like.

A drug delivery system (DDS) refers to a formulation designed to efficiently deliver a required amount of a drug by minimizing the side effects of existing medicines and maximizing efficacy and effectiveness. In particular, the therapeutic efficacy of a drug for treating a mental illness or a central nervous system disorder greatly depends on whether an appropriate amount of a drug is administered at regular intervals such that a sustained level of effective drug concentration for treatment may be generally maintained. There are problems in that when a drug at a relatively high concentration is administered at one time, a dose-dependent side effect frequently occurs, and when the concentration of a drug is reduced to a predetermined level or less between administrations of the drug, the administration efficacy deteriorates and the period during which a patient adapts to the drug may be prolonged.

When a drug treatment is performed with a sustained drug release system, there are advantages in that the administration frequency is reduced, the patient's adaptation to drug is improved, side effects may be prevented, and a therapeutic blood or tissue level of the drug may be maintained for an extended period of time, but a sustained release formulation of a psychopharmaceutical agent, an antidepressant, or a therapeutic agent for a central nervous system disorder has not been developed until now, so that there is an urgent need for an effective drug delivery system.

A microcapsule refers to a capsule having a micrometer unit size, and consists of a capsule wall and a core material embedded in the capsule. Generally, in a microcapsule, the release rate of a core material may be adjusted according to the chemical structure and thickness of a microcapsule wall consisting of a thin synthetic or natural polymer membrane and the particle size of the microcapsule. In this case, as the core material to be used, the type thereof is diverse including a solvent, a flavor, a medicine, and the like, and the application and research in the fields of medicine, food, cosmetics, and the like have been actively conducted according to the use of the core material. However, when the microcapsule is applied to a medicine, it is difficult for the most of the drugs to have a predetermined drug release rate, or the drug is released within a relatively short time. Accordingly, recently, studies to maximize the therapeutic effect by adjusting the release rate of the drug have been actively conducted, and interest in the preparation of a microcapsule for drug delivery using a polymer having characteristics such as biocompatibility and biodegradability has been increasing.

Examples of a representative preparation method of a microcapsule for drug delivery using a polymer include a phase separation method, a solvent extraction method, a solvent evaporation method, a spray drying method, and the like, and characteristics of the microcapsule such as particle size, release characteristics of the drug, and loading rate of the drug are affected by the preparation method, so that an appropriate preparation method should be selected.

Since it is difficult for a microcapsule formulation to have a predetermined drug release rate or the drug is released in the early stage, examples of a method for solving these problems include a method for preparing a microcapsule in which a drug is encapsulated, and then coating the microcapsule as a core with another biodegradable polymer using a fluidized bed particle coating method. Since the core in which the drug is encapsulated is coated with another biodegradable polymer by this method, the ratio at which the encapsulated drug is released in the early stage is decreased.

However, a fluidized bed particle coater, which is equipment used for this method, has a limitation in being commercially or technically applied to expensive drugs, and has difficulties in the process in which the microcapsule should be prepared by two steps even in a production process for actual commercialization.

Therefore, there is a need for developing a new formulation which may suppress the initial release of a drug, sustainably release the drug, adjust the release rate of the drug as desired, has a simple preparation process, and is economically feasible.

DISCLOSURE

Technical Problem

An object of the present invention is to provide a sustained-release drug delivery formulation used by mixing a microcapsule containing a biodegradable polymer and a psychopharmaceutical agent, an antidepressant, or a therapeutic agent for a central nervous system disorder with a hydrogel, and a preparation method thereof.

Further, an object of the present invention is to provide a composition for treating a mental illness and a composition for treating a central nervous system disorder, including the drug delivery formulation.

In addition, an object of the present invention is to suppress excessive initial release of a drug by stepwisely controlling the drug which used to be excessively released from a microcapsule in the early stage by a hydrogel through the drug delivery formulation, and to maximize the therapeutic effect by adjusting the release of a drug at a predetermined rate to maintain the blood drug concentration at a constant level over a long period of time.

Technical Solution

The present invention has been made in an effort to solve the above-described problems, and provides a sustained-release drug delivery formulation for treating a mental illness, including a microcapsule in which a psychopharmaceutical agent or an antidepressant is contained in a biodegradable polymer, and a hydrogel in which a material including a first chemical functional group and a material including a second chemical functional group are crosslinked to each other.

Furthermore, the present invention provides a composition for treating a mental illness, including a microcapsule in which aripiprazole is contained in a biodegradable polymer, and a hydrogel in which methyltetrazine-PEG4-NHS ester and trans-cyclooctene-NHS ester or methyltetrazine-PEG4-NHS amine and trans-cyclooctene-NHS amine are crosslinked to each other.

Further, the present invention provides a sustained-release drug delivery formulation for treating a central nervous system disorder, including a microcapsule in which a drug for treating a central nervous system disorder is contained in a biodegradable polymer, and a hydrogel in which a material including a first chemical functional group and a material including a second chemical functional group are crosslinked to each other.

In addition, the present invention provides a composition for a central nervous system disorder, including a microcapsule in which donepezil is contained in a biodegradable polymer, and a hydrogel in which methyltetrazine-PEG4-NHS ester and trans-cyclooctene-NHS ester or methyltetrazine-PEG4-NHS amine and trans-cyclooctene-NHS amine are crosslinked to each other.

Furthermore, the present invention provides a method for preparing a sustained-release drug delivery formulation for treating a mental illness, the method including steps of (a) preparing a drug dispersion solution by dissolving a biodegradable polymer having a molecular weight of 10,000 to 200,000 g/mol and a psychopharmaceutical agent or an antidepressant in a solvent, (b) injecting the drug dispersion solution into a single axis ultrasonic sprayer or a syringe, (c) preparing a microcapsule by spraying the drug dispersion solution from the single axis ultrasonic sprayer or the syringe, (d) performing a crosslinking reaction by adding a material including a first chemical functional group and a material including a second chemical functional group to a hydrogel solution, and (e) dispersing the microcapsule containing the drug in the crosslinked hydrogel solution.

Further, the present invention provides a method for preparing a sustained-release drug delivery preparation for treating a central nervous system disorder, the method including steps of (a) preparing a drug dispersion solution by dissolving a biodegradable polymer having a molecular weight of 10,000 to 200,000 g/mol and a therapeutic agent for a central nervous system disorder in a solvent, (b) injecting the drug dispersion solution into a single axis ultrasonic sprayer or a syringe, (c) preparing a microcapsule by spraying the drug dispersion solution from the single axis ultrasonic sprayer or the syringe, (d) performing a crosslinking reaction by adding a material including a first chemical functional group and a material including a second chemical functional group to a hydrogel solution, and (e) dispersing the microcapsule containing the drug in the crosslinked hydrogel solution.

Advantageous Effects

A drug delivery formulation for treating a mental illness or a central nervous system disorder according to the present invention can slowly release a drug at a constant rate without a burst of drug release in the early stage of drug administration to maintain a constant blood drug level over a long period of time and thus enjoys the advantage of preventing excessive initial release of a drug, which is a problem with the administration of conventional psychopharmaceutical agents, antidepressants, or therapeutic agents for a central nervous system disorder, and easily obtaining a desirable sustained release behavior by single administration without the need for multiple administrations divided at regular time intervals. In addition, a method for preparing a drug delivery formulation according to the present invention is a process simpler than conventional methods and has the advantage of reducing time and costs in preparing a sustained-release drug delivery formulation.

MODES OF THE INVENTION

Figure 1:
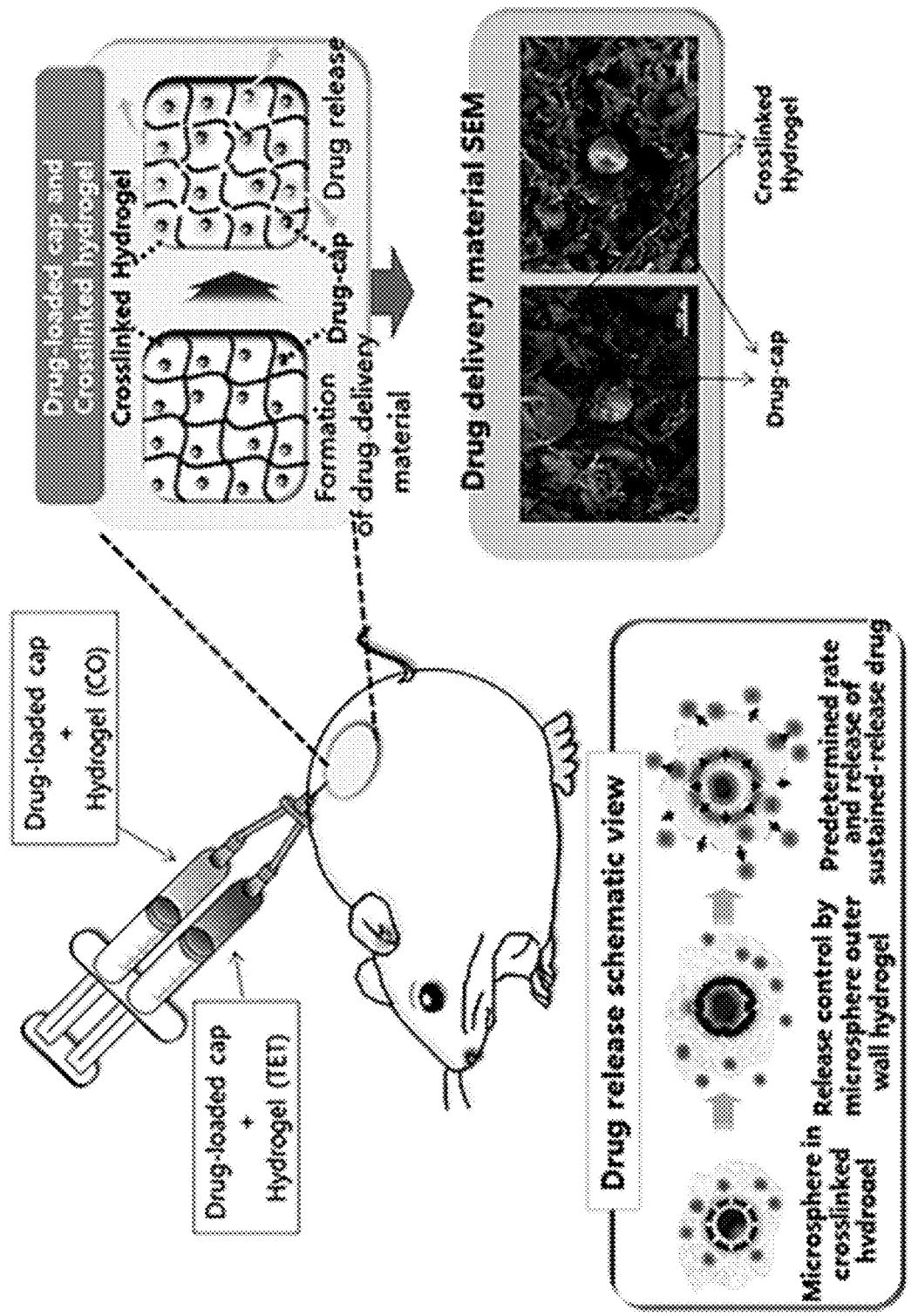
FIG. 1 is a schematic view of a method for injecting a drug delivery formulation and a drug release according to an embodiment of the present invention.

The present invention as described above will be described in more detail as follows.

The present invention relates to a drug delivery system for initial release control and stepwise release of a drug for treating a mental illness or a central nervous system, and more particularly, to a drug delivery formulation, wherein a microcapsule in which a drug is encapsulated is primarily prepared, and then the release amount and rate of a drug are secondarily adjusted, in order to overcome excessive initial release or a rapid decrease or increase in release amount over time.

Therefore, the sustained-release drug delivery formulation for treating a mental illness of the present invention is characterized by including a microcapsule in which a psychopharmaceutical agent or an antidepressant is contained in a biodegradable polymer and a hydrogel in which a material including a first chemical functional group and a material including a second chemical functional group are crosslinked to each other.

Therefore, the sustained-release drug delivery formulation for treating a central nervous system disorder of the present invention is characterized by including a microcapsule in which a drug for treating a central nervous system disorder is contained in a biodegradable polymer and a hydrogel in which a material including a first chemical functional group and a material including a second chemical functional group are crosslinked to each other.

The method for preparing a sustained-release drug delivery formulation for treating a mental illness of the present invention is characterized by including steps of (a) preparing a drug dispersion solution by dissolving a biodegradable polymer having a molecular weight of 10,000 to 200,000 g/mol and a psychopharmaceutical agent or an antidepressant in a solvent, (b) injecting the drug dispersion solution into a single axis ultrasonic sprayer or a syringe, (c) preparing a microcapsule by spraying the drug dispersion solution from the single axis ultrasonic sprayer or the syringe, (d) performing a crosslinking reaction by adding a material including a first chemical functional group and a material including a second chemical functional group to a hydrogel solution, and (e) dispersing the microcapsule containing the drug in the crosslinked hydrogel solution.

The method for preparing a sustained-release drug delivery formulation for treating a central nervous system disorder of the present invention is characterized by including steps of (a) preparing a drug dispersion solution by dissolving a biodegradable polymer having a molecular weight of 10,000 to 200,000 g/mol and a therapeutic agent for treating a central nervous system disorder in a solvent, (b) injecting the drug dispersion solution into a single axis ultrasonic sprayer or a syringe, (c) preparing a microcapsule by spraying the drug dispersion solution from the single axis ultrasonic sprayer or the syringe, (d) performing a crosslinking reaction by adding a material including a first chemical functional group and a material including a second chemical functional group to a hydrogel solution, and (e) dispersing the microcapsule containing the drug in the crosslinked hydrogel solution.

The biodegradable polymer used in the present invention is used as an outer wall material (shell) surrounding a microcapsule, and the drug release rate is primarily controlled according to the type and composition of biodegradable polymer. A psychopharmaceutical agent, an antidepressant, or a drug for treating a central nervous system disorder is encapsulated as a core material (core) in the biodegradable polymer to form a microcapsule. In the present invention, the biodegradable polymer, which is biocompatible and has biodegradable characteristics, is used as a wall of a microcapsule, and the release amount and rate of a drug may be primarily controlled according to the type and combination of polymer.

The biodegradable polymer used in the present invention includes a synthetic polymer such as polyethylene glycol (PEG), caprolactone (CL), glycolide (GA), lactide (LA), polycaprolactone, polyalkyl carbonate, polyamino acid, polyhydroxybutyric acid, polyorthoester, polyanhydrides, poly(ethylene oxide)poly(propylene oxide)poly(ethylene oxide) (pluronic), polylactide (PLA), polyglycolide (PGA) or polylactide-co-glycolide (PLGA) which is a copolymer thereof and polylactide-co-glycolide-glucose (PLGA-glucose) which is a molded polymer thereof, and a polyester such as methoxy polyethylene glycol-(polycaprolactone-co-polylactide) (MPEG-(PCL-co-PLLA)) and a natural polymer such as carboxymethyl cellulose, algin, alginic acid, alginate, hyaluronic acid, polypeptides, proteins, gelatin, casein, chitin derivatives, chitosan, and small intestinal submucosa.

As the biodegradable polymer, polylactide-co-glycolide (PLGA) may be preferably used.

The release amount and rate of a drug may be controlled according to the type and combination of biodegradable polymer. For example, the rate at which polylactide-co-glycolide (PLGA) is degraded in the human body depends on the ingredient ratio of polylactide (PLA) and polyglycolide (PGA), and the release rate of a drug can be adjusted by the ingredient ratio. Therefore, when the biodegradable polymer is used as a matrix for adjusting the release of a drug, the release rate of a drug may be controlled.

In addition, since the release rate of a drug varies depending on the molecular weight of the biodegradable polymer, a biodegradable polymer having a molecular weight of 10,000 to 200,000 g/mol, preferably 30,000 to 90,000 g/mol may be used. As a polymer having a low molecular weight is used, the drug is released too quickly, and when a polymer having a high molecular weight is used, the drug is released too slowly. Therefore, in preparing a microcapsule and controlling the release using the microcapsule, it is important to select a polymer having an appropriate molecular weight and prepare a microcapsule.

Among the biodegradable polymers, polylactide-co-glycolide (PLGA) was approved by the US Food and Drug Administration (FDA) as a non-toxic biodegradable polymer that can be used for the human body, and has been widely used as a material for tissue regeneration in the human body, a carrier for drug delivery, or a surgical suture, and its biocompatibility has already been proven.

A drug used for the drug delivery formulation of the present invention is not limited in type as long as the drug is used as a psychopharmaceutical agent, an antidepressant, or a therapeutic agent for a central nervous system disorder.

A drug-encapsulating microcapsule may be prepared by incorporating the drug into the biodegradable polymer. The microcapsule may further include one or more additives such as an antiseptic, a preservative, and an excipient. The incorporation process may be performed by a method for preparing a microcapsule using a single axis ultrasonic spray method [B. S. Kim, J. M. Oh, K. S. Kim et al, Biomaterials, 30, 902 (2009); B. S. Kim, J. M. Oh, H. Hyun et al, MOLECULAR PHARMACEUTICS, 6, 353 (2009)] or a syringe. Through the single axis ultrasonic spray method, it is possible to prepare a microcapsule having a dual structure in which a composition of a core part is different from a composition of an outer part with which the core part is coated, and in this case, there are advantages in that the content of the drug in the microcapsule is 60 to 70%, an excellent drug encapsulation rate is exhibited, and the initial release amount is also suppressed.

However, there is still a problem in that a portion of a drug is excessively released in the early stage only by the method, so that in order to solve the problem and simultaneously adjust the release amount on a sustained basis, the present invention is characterized by preparing a drug delivery preparation by additionally mixing the prepared microcapsule with a hydrogel.

An in vivo injectable hydrogel is an intelligent hydrogel that can be used without surgery, and generally, the injectable hydrogel has characteristics such as in vitro fluidity, so that the hydrogel can be implanted using a syringe, and after the in vivo injection, gelation occurs. The in vivo injectable hydrogel of the present invention may be prepared using a synthetic and natural polymer such as hyaluronic acid, polyacrylamide, poly(N-isopropylacrylamide), β-glycerophosphate, poly(ethylene oxide)poly(propylene oxide)poly(ethylene oxide) (pluronic), polycaprolactone, polyethylene glycol, methoxy ethylene glycol-polycaprolactone (MPEG-PCL), carboxymethylcellulose (CMC), a mixture of carboxymethylcellulose (CMC) and polyethyleneimine (PEI), algin, alginic acid, alginate, polypeptides, proteins, gelatin, casein, chitin derivatives, chitosan, and small intestinal submucosa. The polymer may be put into a phosphate buffer solution, and the like, and prepared into a hydrogel, but the preparation method is not limited thereto, and various preparation methods may be used according to the type of polymer.

The hydrogel of the present invention is characterized in that a material including a first chemical functional group and a material including a second chemical functional group are crosslinked to each other. The first chemical functional group and the second chemical functional group are chemically reacted in the hydrogel to be crosslinked, which allows the hydrogel to be formed as an effective drug delivery support. The microcapsule containing the drug in the crosslinked hydrogel may be uniformly dispersed and immobilized, thereby maximizing an effect that the drug is released from the formulation over a long period of time when the drug delivery formulation of the present invention is injected in vivo.

The material including the first chemical functional group of the present invention is characterized by being one or more selected from the group consisting of amino-PEG4-alkyne, alkyne-PEG5-acid, alkyne-PEG-amine, oxiranylamine, 2-oxiranyl-ethylamine, acrylamide, acrylic acid, acryloyl chloride, methyltetrazine-amine, methyltetrazine-PEG4-amine, methyltetrazine-propylamine, tetrazine-PEG5-NHS ester, methyltetrazine-PEG4-NHS ester, methyltetrazine-PEG4-NHS amine, methyltetrazine-silfo-NHS ester, methyltetrazine-PEG4-acid, methyltetrazine-PEG12-NHS ester, methyltetrazine-NHS ester, methyltetrazine-acid, and tetrazine-acid, and the material including the second chemical functional group of the present invention is characterized by being one or more selected from the group consisting of azide-PEG4-amine, 3-amino-1-propanethiol, 11-mercaptoundecanoic acid, Amino-methanethiol, thiol PEG amine, ethylene diamine, PEG diamine, (S)-3-amino-2-(hydroxymethyl)propionic acid, amino-acetic acid, trans-cyclooctene-amine, trans-cyclooctene-NHS ester, trans-cyclooctene-NHS amine, trans cyclooctene-PEG-NHS ester, and trans cyclooctene-PEG4-acid.

In the present invention, it is preferred that the hydrogel and materials including the first and second chemical functional groups are mixed at a molar ratio of 1:400 to 1:600, but the molar ratio is not limited thereto. When the range is less than 1:400, there is a problem in that the mechanical strength of the drug delivery formulation is lowered, and when the range is more than 1:600, there is a problem in that the transport of a microcapsule containing the drug and the drug release may be limited by an excessive crosslinking degree.

Further, it is preferred that the hydrogel in which the material including the first chemical functional group and the material including the second chemical functional group are crosslinked to each other has a biopolymer concentration of 1 to 30 wt %. When the polymer concentration is less than 1 wt %, it is difficult to maintain a gel form during the subcutaneous injection of the drug delivery formulation, and when the polymer concentration is more than 30 wt %, the viscosity is excessively increased, so that undesirable physical properties as a drug delivery formulation may be exhibited.

According to another embodiment of the present invention, the drug delivery formulation may further include a solvent of acetic acid, distilled water, or a buffer solution, but the solvent is not limited thereto. Specifically, it is preferred that the buffer solution is one or more selected from 2-(n-morpholino)ethanesulfonic acid, 4-(4,6-dimethoxy-1,3,5-tiazin-2-yl)-4-methylmorpholinium chloride, and phosphate buffered saline.

The drug delivery formulation according to the present invention may be used in the form of an injectable, but the form is not limited thereto.

An embodiment of the present invention may include a drug delivery formulation containing aripiprazole as a psychopharmaceutical agent, and provides a composition for treating a mental illness, including a microcapsule in which aripiprazole is contained in a biodegradable polymer, and a hydrogel in which methyltetrazine-PEG4-NHS ester and trans-cyclooctene-NHS ester or methyltetrazine-PEG4-NHS amine and trans-cyclooctene-NHS amine are crosslinked to each other.

Another embodiment of the present invention may include a drug delivery formulation containing donepezil as a therapeutic agent for a central nervous system disorder, and provides a composition for treating a central nervous system disorder, including a microcapsule in which donepezil is contained in a biodegradable polymer, and a hydrogel in which methyltetrazine-PEG4-NHS ester and trans-cyclooctene-NHS ester or methyltetrazine-PEG4-NHS amine and trans-cyclooctene-NHS amine are crosslinked to each other.

Hereinafter, preferred Examples for helping the understanding of the present invention will be suggested. However, the following Examples are provided only to more easily understand the present invention, and the contents of the present invention are not limited by the following Examples.

Example 1: Preparation of Microcapsule Encapsulating Anhydrous Aripiprazole (Solvent Condition)

1-1. Preparation of Microcapsule Using Methylene Chloride (MC) as Solvent

A uniform drug dispersion solution was prepared by dissolving a poly(lactic-co-glycolic acid) (PLGA) having a molecular weight of 33,000 g/mol in methylene chloride (MC) so as to have a concentration of 3 wt % and dissolving 2 wt % of anhydrous aripiprazole. After the solution was put into a syringe, the solution was flowed through a single axis ultrasonic sprayer at a flow rate of 4 ml/min at room temperature. A microcapsule was formed by preparing 250 ml of an aqueous polyvinyl alcohol (PVA) solution, which is a 0.5 wt % aqueous solution, and spraying the drug dispersion solution at a vibration frequency of 60 Hz to disperse the drug dispersion solution in the aqueous polyvinyl alcohol solution. After the aqueous polyvinyl alcohol solution was stirred at 700 rpm at room temperature for 2 hours and stabilized, the resulting microcapsule was put into distilled water, washed four to five times, and freeze-dried, thereby obtaining a microcapsule in which anhydrous aripiprazole was encapsulated.

1-2. Preparation of Microcapsule Using Chloroform as Solvent

A microcapsule in which anhydrous aripiprazole was encapsulated was prepared in the same manner as in Example 1-1, except that as the solvent in Example 1-1, chloroform was used instead of methylene chloride (MC).

1-3. Preparation of Microcapsule Using Ethyl Acetate (EA) as Solvent

A microcapsule in which anhydrous aripiprazole was encapsulated was prepared in the same manner as in Example 1-1, except that as the solvent in Example 1-1, ethyl acetate (EA) was used instead of methylene chloride (MC).

1-4. Analysis of Characteristics of Microcapsule

Figure 2:
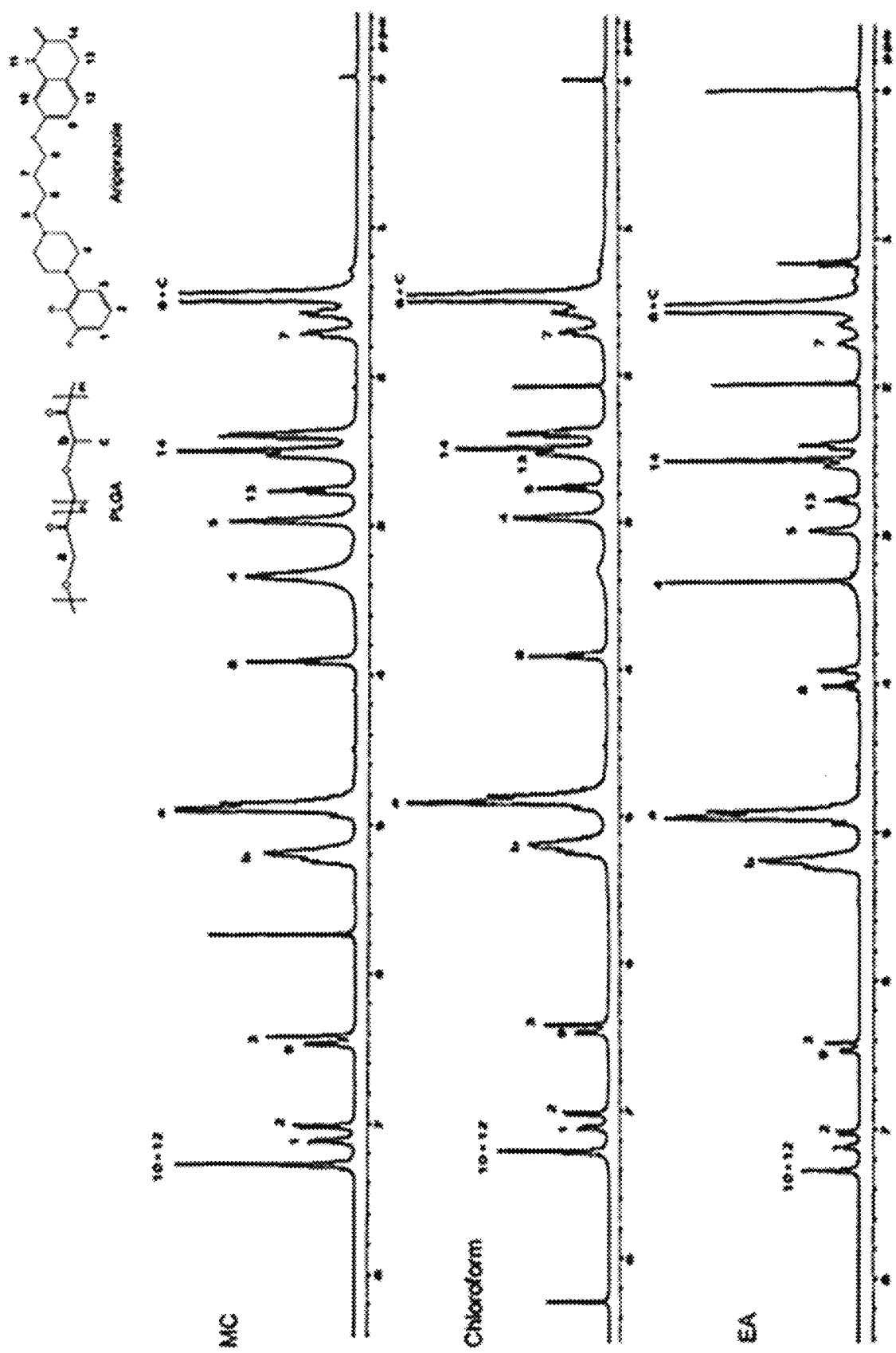
FIG. 2 is a set of 1H-NMR analysis results of a microcapsule containing anhydrous aripiprazole prepared by varying solvents according to an embodiment of the present invention.

As a result of measuring the microcapsules prepared by varying solvents of the drug dispersion solutions in Examples 1-1 to 1-3 using 1H-NMR, it could be confirmed that respective microcapsules in which anhydrous aripiprazole was encapsulated in polylactide-co-glycolide (PLGA) were prepared (FIG. 2).

Figure 3:
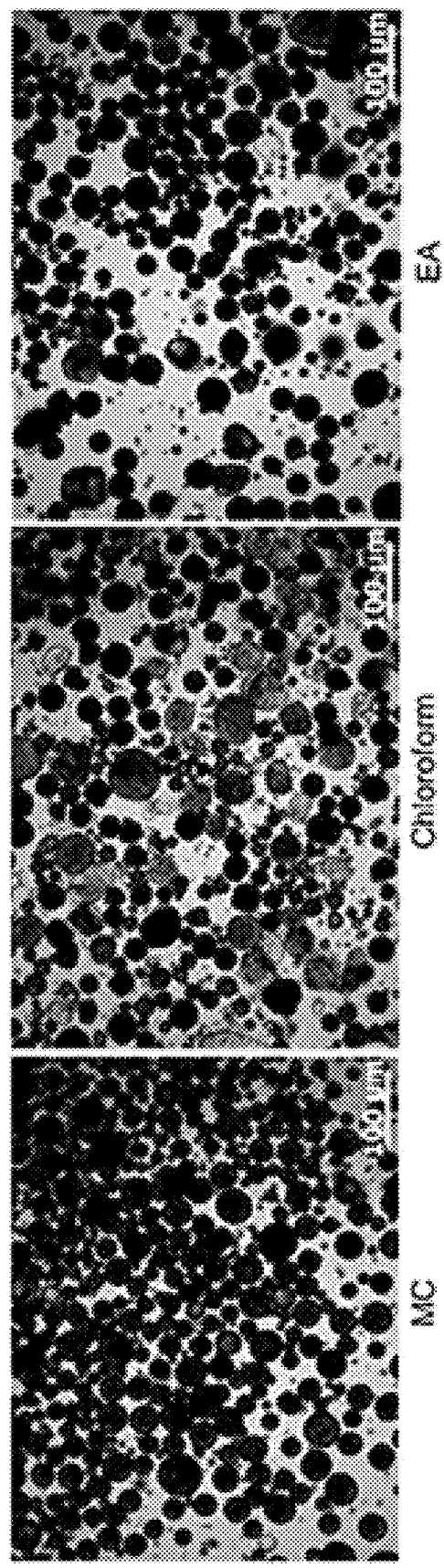
FIG. 3 is a set of particle size optical microscope images of a microcapsule containing anhydrous aripiprazole prepared by varying solvents.

In addition, after 10 mg of each prepared microcapsule was suspended in distilled water, the particle sizes of the microcapsules were measured and the optical microscope images were confirmed using a Zeta potential & Particle size analyzer. In consideration of the error range, the particle size values measured repeatedly three times are shown in the following Table 1, and the optical microscope images of the microcapsules are shown in FIG. 3.

TABLE 1

|  | MC | Chloroform | EA |
|---|---|---|---|
| Particle size (μm) | 91.09 ± 2.89 | 84.06 ± 5.90 | 71.59 ± 2.35 |

In order to observe the preparation efficiency of the microcapsule according to the preparation method varying the solvents, the yield and encapsulation efficiency of the microcapsule in which anhydrous aripiprazole was encapsulated were measured.

Specifically, the yields of the microcapsules prepared in Examples 1-1 to 1-3 were compared with the amounts added by measuring the entire weight of the microcapsules, and the encapsulation efficiency of the microcapsule was calculated using [encapsulation efficiency=(drug content of the resulting aripiprazole capsule/drug content of the theoretical aripiprazole capsule)×100].

The 'drug content of the resulting aripiprazole capsule' was measured by comparing the PLGA area value peak (δ=4.8 to 4 ppm, 5 to 5.4 ppm) with the anhydrous aripiprazole area value peak (δ=7.1 ppm) from a result of measurement using 1H-NMR after dissolving a microcapsule to which a reference material was added in DMSO. As another method, the 'drug content of the resulting aripiprazole capsule' was measured using high performance liquid chromatography (HPLC) (Agilent-1200, USA) after 10 mg of the microcapsule was taken, dissolved in a mobile phase, and filtered. As the measurement conditions of HPLC, a C18 column (5 μm, 4.6×250 mm I.D.) (Thermo Scientific) was used, detection was performed at a wavelength of 254 nm, the mobile phase was aqueous anhydrous sodium sulfate solution:acetonitrile:methanol:acetic acid=56:33:11:1 (v/v), the flow rate was 1 ml/min, the injection volume was 100 μl, and the drug content was measured at 25° C.

The yield and encapsulation efficiency of the microcapsule and the amount of the drug in 10 mg of the capsule are shown in the following Table 2.

TABLE 2

|  | Yield (%) | Encapsulation efficiency (%) | Amount (mg) of drug per 10 mg of capsule |
|---|---|---|---|
| MC | 88 | 65.0 | 2.6 |
| Chloroform | 86 | 52.5 | 2.1 |
| EA | 81 | 35.0 | 1.4 |

As a result of analyzing characteristics of the microcapsules prepared in Examples 1-1 to 1-3, it could be confirmed that the yield and encapsulation efficiency of the microcapsule using methylene chloride as a solvent and the content of the drug in the capsule were the highest, and a microcapsule with a relatively uniform size was prepared.

Example 2: Preparation of Microcapsule Encapsulating Anhydrous Aripiprazole (Temperature Condition)

2-1. Preparation of Microcapsule at Room Temperature

A uniform drug dispersion solution was prepared by dissolving polylactide-co-glycolide (PLGA) having a molecular weight of 33,000 g/mol in methylene chloride (MC) so as to have a concentration of 3 wt % and dissolving 2 wt % of anhydrous aripiprazole. After the solution was put into a syringe, the solution was flowed through a single axis ultrasonic sprayer at a flow rate of 4 ml/min at room temperature. A microcapsule was formed by preparing 250 ml of an aqueous polyvinyl alcohol (PVA) solution, which is a 0.5 wt % aqueous solution, and spraying the drug dispersion solution at a vibration frequency of 60 Hz to disperse the drug dispersion solution in the aqueous polyvinyl alcohol solution. After the aqueous polyvinyl alcohol solution was stirred at 700 rpm at room temperature for 2 hours and stabilized, the resulting microcapsule was put into distilled water, washed four to five times, and freeze-dried, thereby obtaining a microcapsule in which anhydrous aripiprazole was encapsulated.

2-2. Preparation of Microcapsule at 30° C.

A microcapsule encapsulating anhydrous aripiprazole was prepared in the same manner as in Example 2-1, except that in Example 2-1, the temperature at which the drug dispersion solution was injected into the single axis ultrasonic sprayer was set to 30° C.

2-3. Preparation of Microcapsule at 35° C.

A microcapsule encapsulating anhydrous aripiprazole was prepared in the same manner as in Example 2-1, except that in Example 2-1, the temperature at which the drug dispersion solution was injected into the single axis ultrasonic sprayer was set to 35° C.

2-4. Preparation of Microcapsule at 40° C.

A microcapsule encapsulating anhydrous aripiprazole was prepared in the same manner as in Example 2-1, except that in Example 2-1, the temperature at which the drug dispersion solution was injected into the single axis ultrasonic sprayer was set to 40° C.

2-5. Analysis of Characteristics of Microcapsule

Figure 4:
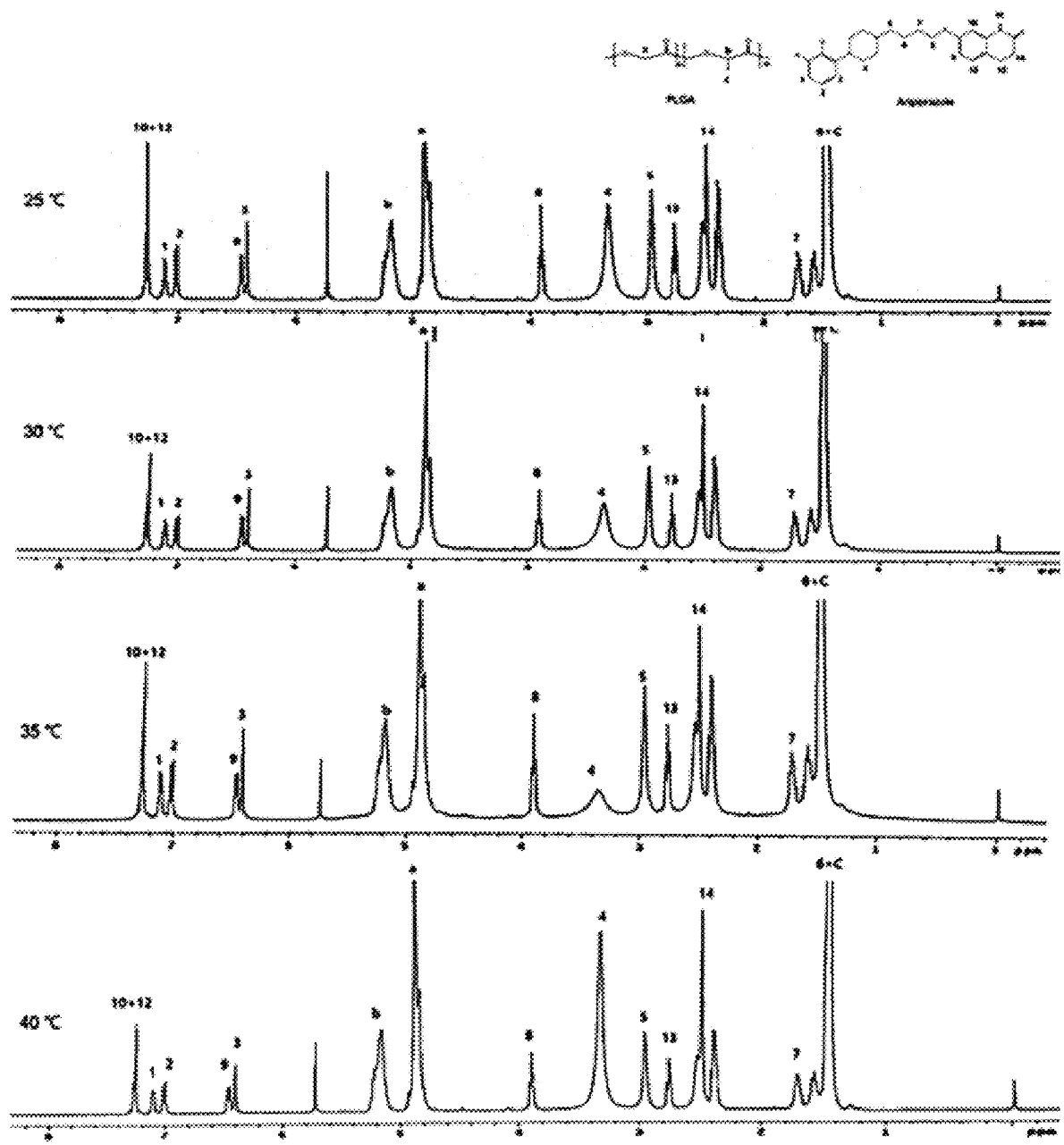
FIG. 4 is a set of 1H-NMR analysis results of a microcapsule containing anhydrous aripiprazole prepared by varying the temperature of a solution according to an embodiment of the present invention.

As a result of measuring the microcapsules prepared by varying solvents of the drug dispersion solutions in Examples 2-1 to 2-4 using 1H-NMR, it could be confirmed that respective microcapsules in which anhydrous aripiprazole was encapsulated in polylactide-co-glycolide (PLGA) were prepared (FIG. 4).

Figure 5:
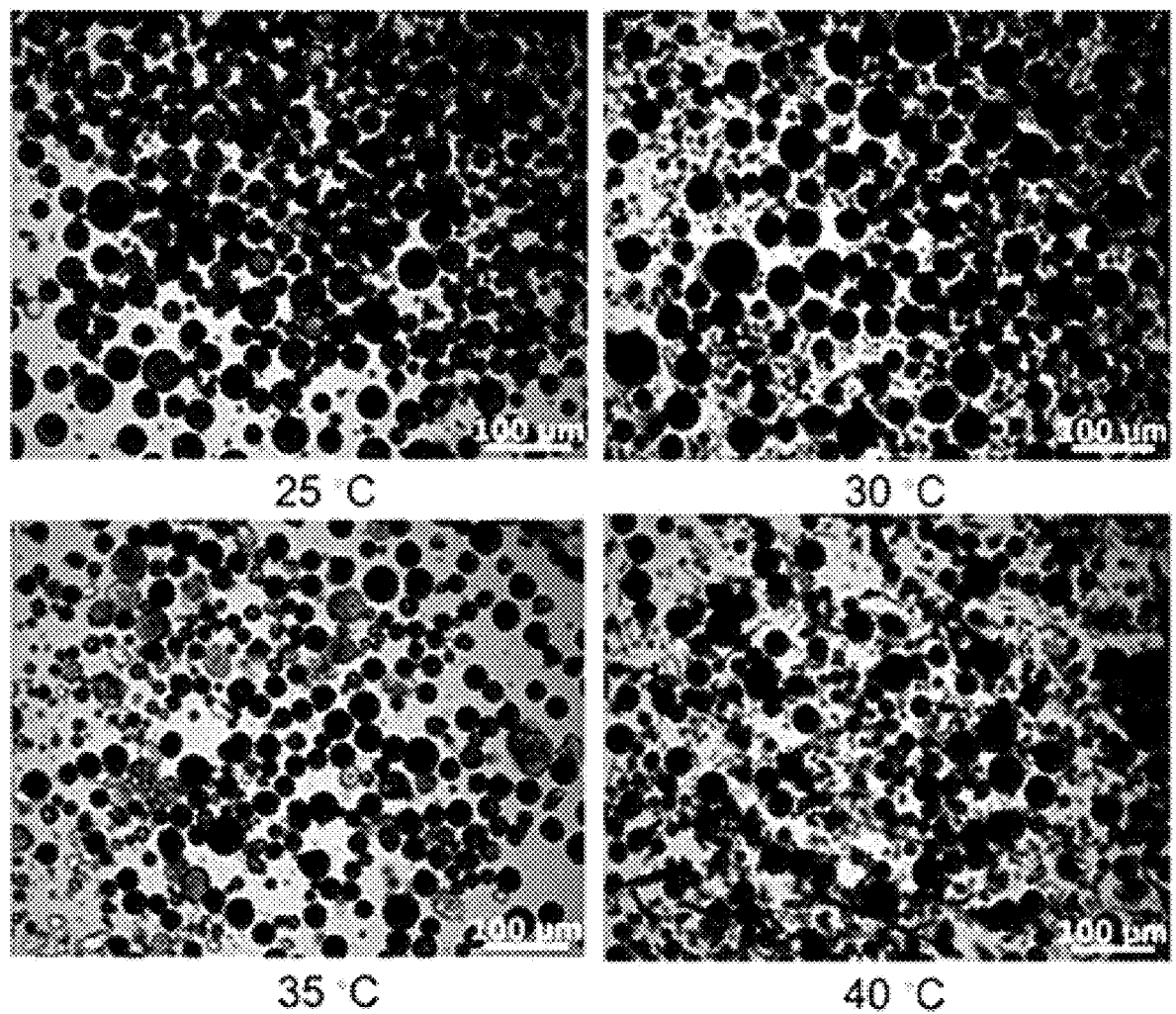
FIG. 5 is a set of particle size optical microscope images of a microcapsule containing anhydrous aripiprazole prepared by varying the temperature of a solution.

In addition, after 10 mg of each prepared microcapsules was suspended in distilled water, the particle sizes of the microcapsules were measured and the optical microscope images were confirmed using a Zeta potential & Particle size analyzer. In consideration of the error range, the particle size values measured repeatedly three times are shown in the following Table 3, and the optical microscope images are shown in FIG. 5.

TABLE 3

| | 25° C. | 30° C. | 35° C. | 40° C. |
|---|---|---|---|---|
| Particle size (μm) | 91.09 ± 2.89 | 38.51 ± 6.83 | 17.16 ± 4.21 | 15.65 ± 2.38 |

In order to observe the preparation efficiency of the microcapsule according to the preparation method varying the temperature of the drug dispersion solution, the yield and encapsulation efficiency of the microcapsule in which anhydrous aripiprazole was encapsulated were measured.

Specifically, the yields of the microcapsules prepared in Examples 2-1 to 2-4 were compared with the amounts added by measuring the entire weight of the microcapsules, and the encapsulation efficiency of the microcapsule was calculated using [encapsulation efficiency=(drug content of the resulting aripiprazole capsule/drug content of the theoretical aripiprazole capsule)×100].

The 'drug content of the resulting aripiprazole capsule' was measured by comparing the PLGA area value peak ($\delta$=4.8 to 4 ppm, 5 to 5.4 ppm) with the anhydrous aripiprazole area value peak ($\delta$=7.1 ppm) from a result of measurement using 1H-NMR after dissolving a microcapsule to which a reference material was added in DMSO. As another method, the 'drug content of the resulting aripiprazole capsule' was measured using HPLC (Agilent-1200, USA) after 10 mg of the microcapsule was taken, dissolved in a mobile phase, and filtered. As the measurement conditions of HPLC, a C18 column (5 μm, 4.6×250 mm I.D.) (Thermo Scientific) was used, detection was performed at a wavelength of 254 nm, the mobile phase was aqueous anhydrous sodium sulfate solution:acetonitrile:methanol:acetic acid=56:33:11:1 (v/v), the flow rate was 1 ml/min, the injection volume was 100 μl, and the drug content was measured at 25° C.

The yield and encapsulation efficiency of the microcapsule and the amount of the drug in 10 mg of the capsule are shown in the following Table 4.

TABLE 4

| | Yield (%) | Encapsulation efficiency (%) | Amount (mg) of drug per 10 mg of capsule |
|---|---|---|---|
| 25° C. | 88 | 65.0 | 2.6 |
| 30° C. | 87 | 55.0 | 2.2 |
| 35° C. | 89 | 60.0 | 2.4 |
| 40° C. | 75 | 57.5 | 2.3 |

As a result of analyzing characteristics of the microcapsules prepared in Examples 2-1 to 2-4, it could be confirmed that the yield and encapsulation efficiency of the microcapsule prepared at 25° C. and the content of the drug in the capsule were the highest, and a microcapsule with a relatively uniform size was prepared.

Example 3: Preparation of Microcapsule Encapsulating Monohydrate Aripiprazole (Solvent Condition)

3-1. Preparation of Microcapsule Using Methylene Chloride (MC) as Solvent

A uniform drug dispersion solution was prepared by dissolving polylactide-co-glycolide (PLGA) having a molecular weight of 33,000 g/mol in methylene chloride (MC) so as to have a concentration of 3 wt % and dissolving 2 wt % of aripiprazole. After the solution was put into a syringe, the solution was flowed through a single axis ultrasonic sprayer at a flow rate of 4 ml/min at room temperature. A microcapsule was formed by preparing 250 ml of an aqueous polyvinyl alcohol (PVA) solution, which is a 0.5 wt % aqueous solution, and spraying the drug dispersion solution at a vibration frequency of 60 Hz to disperse the drug dispersion solution in the aqueous polyvinyl alcohol solution. After the aqueous polyvinyl alcohol solution was stirred at 700 rpm at room temperature for 2 hours and stabilized, the resulting microcapsule was put into distilled water, washed four to five times, and freeze-dried, thereby obtaining a microcapsule in which aripiprazole was encapsulated.

3-2. Preparation of Microcapsule Using Tetrahydrofuran (THF) as Solvent

A microcapsule in which aripiprazole was encapsulated was prepared in the same manner as in Example 3-1, except that as the solvent in Example 3-1, tetrahydrofuran (THF) was used instead of methylene chloride (MC).

3-3. Preparation of Microcapsule Using Ethyl Acetate (EA) as Solvent

A microcapsule in which aripiprazole was encapsulated was prepared in the same manner as in Example 3-1, except that as the solvent in Example 3-1, ethyl acetate (EA) was used instead of methylene chloride (MC).

3-4. Analysis of Characteristics of Microcapsule

Figure 6:
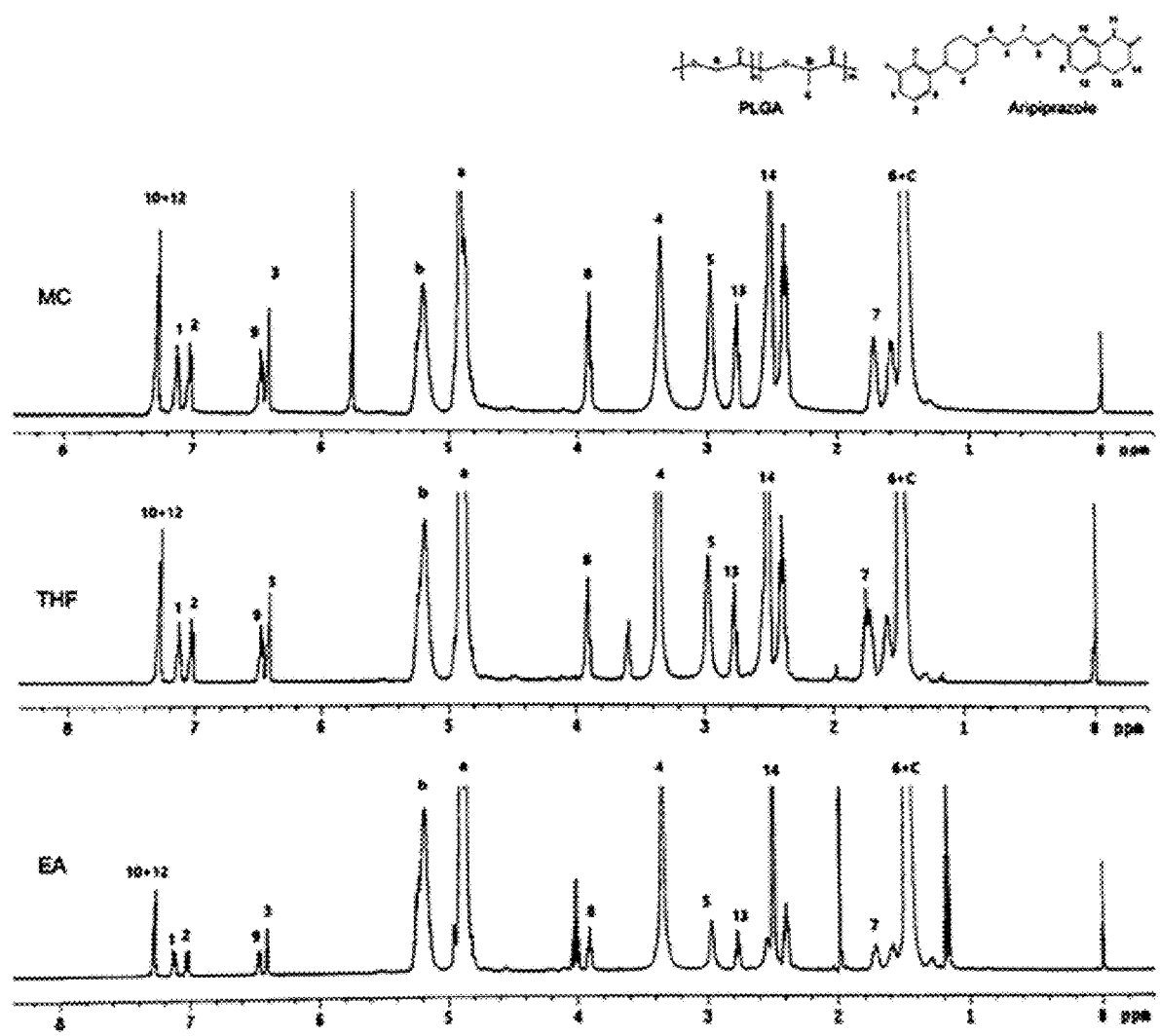
FIG. 6 is a set of 1H-NMR analysis results of a microcapsule containing aripiprazole prepared by varying solvents of a solution according to an embodiment of the present invention.

As a result of measuring the microcapsules prepared by varying solvents of the drug dispersion solutions in Examples 3-1 to 3-3 using 1H-NMR, it could be confirmed that respective microcapsules in which aripiprazole was encapsulated in polylactide-co-glycolide (PLGA) were prepared (FIG. 6).

Figure 7:
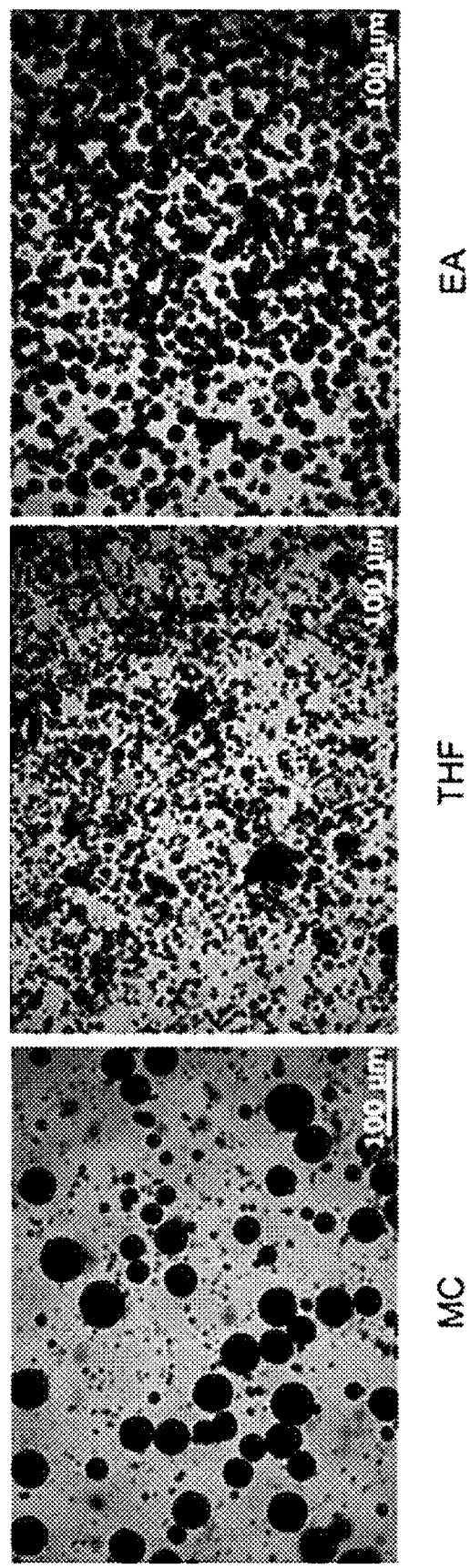
FIG. 7 is a set of particle size optical microscope images of a microcapsule containing aripiprazole prepared by varying solvents.

In addition, after 10 mg of each prepared microcapsules was suspended in distilled water, the particle sizes of the microcapsules were measured and the optical microscope images were confirmed using a Zeta potential & Particle size analyzer. In consideration of the error range, the particle size values measured repeatedly three times are shown in the following Table 5, and the optical microscope images are shown in FIG. 7.

TABLE 5

|  | MC | THF | EA |
|---|---|---|---|
| Particle size (μm) | 80.67 ± 3.97 | 7.31 ± 0.49 | 12.56 ± 3.91 |

In order to observe the preparation efficiency of the microcapsule according to the preparation method varying the solvents, the yield and encapsulation efficiency of the microcapsule in which aripiprazole was encapsulated were measured.

Specifically, the yields of the microcapsules prepared in Examples 3-1 to 3-3 were compared with the amounts added by measuring the entire weight of the microcapsules, and the encapsulation efficiency of the microcapsule was calculated using [encapsulation efficiency=(drug content of the resulting aripiprazole capsule/drug content of the theoretical aripiprazole capsule)×100].

The 'drug content of the resulting aripiprazole capsule' was measured by comparing the PLGA area value peak (δ=4.8 to 4 ppm, 5 to 5.4 ppm) with the anhydrous aripiprazole area value peak (δ=7.1 ppm) from a result of measurement using 1H-NMR after dissolving a microcapsule to which a reference material was added in DMSO. As another method, the 'drug content of the resulting aripiprazole capsule' was measured using HPLC (Agilent-1200, USA) after 10 mg of the microcapsule was taken, dissolved in a mobile phase, and filtered. As the measurement conditions of HPLC, a C18 column (5 μm, 4.6×250 mm I.D.) (Thermo Scientific) was used, detection was performed at a wavelength of 254 nm, the mobile phase was aqueous anhydrous sodium sulfate solution:acetonitrile:methanol:acetic acid=56:33:11:1 (v/v), the flow rate was 1 ml/min, the injection volume was 100 μl, and the drug content was measured at 25° C.

The yield and encapsulation efficiency of the microcapsule and the amount of the drug in 10 mg of the capsule are shown in the following Table 6.

TABLE 6

|  | Yield (%) | Encapsulation efficiency (%) | Amount (mg) of drug per 10 mg of capsule |
|---|---|---|---|
| MC | 88 | 90.0 | 3.6 |
| THF | 49 | 80.0 | 3.2 |
| EA | 84 | 62.5 | 2.5 |

As a result of analyzing characteristics of the microcapsules prepared in Examples 3-1 to 3-3, it could be confirmed that the yield and encapsulation efficiency of the microcapsule using methylene chloride as a solvent and the content of the drug in the capsule were the highest, and a microcapsule with a relatively uniform size was prepared.

Example 4: Preparation of Microcapsule Encapsulating Monohydrate Aripiprazole (Temperature Condition)

4-1. Preparation of Microcapsule at Room Temperature

A uniform drug dispersion solution was prepared by dissolving polylactide-co-glycolide (PLGA) having a molecular weight of 33,000 g/mol in methylene chloride (MC) so as to have a concentration of 3 wt % and dissolving 2 wt % of aripiprazole. After the solution was put into a syringe, the solution was flowed through a single axis ultrasonic sprayer at a flow rate of 4 ml/min at room temperature. A microcapsule was formed by preparing 250 ml of an aqueous polyvinyl alcohol (PVA) solution, which is a 0.5 wt % aqueous solution, and spraying the drug dispersion solution at a vibration frequency of 60 Hz to disperse the drug dispersion solution in the aqueous polyvinyl alcohol solution. After the aqueous polyvinyl alcohol solution was stirred at 700 rpm at room temperature for 2 hours and stabilized, the resulting microcapsule was put into distilled water, washed four to five times, and freeze-dried, thereby obtaining a microcapsule in which aripiprazole was encapsulated.

4-2. Preparation of Microcapsule at 30° C.

A microcapsule encapsulating aripiprazole was prepared in the same manner as in Example 4-1, except that in Example 4-1, the temperature at which the drug dispersion solution was injected into the single axis ultrasonic sprayer was set to 30° C.

4-3. Preparation of Microcapsule at 35° C.

A microcapsule encapsulating aripiprazole was prepared in the same manner as in Example 4-1, except that in Example 4-1, the temperature at which the drug dispersion solution was injected into the single axis ultrasonic sprayer was set to 35° C.

4-4. Preparation of Microcapsule at 40° C.

A microcapsule encapsulating aripiprazole was prepared in the same manner as in Example 4-1, except that in Example 4-1, the temperature at which the drug dispersion solution was injected into the single axis ultrasonic sprayer was set to 40° C.

4-5. Analysis of Characteristics of Microcapsule

Figure 8:
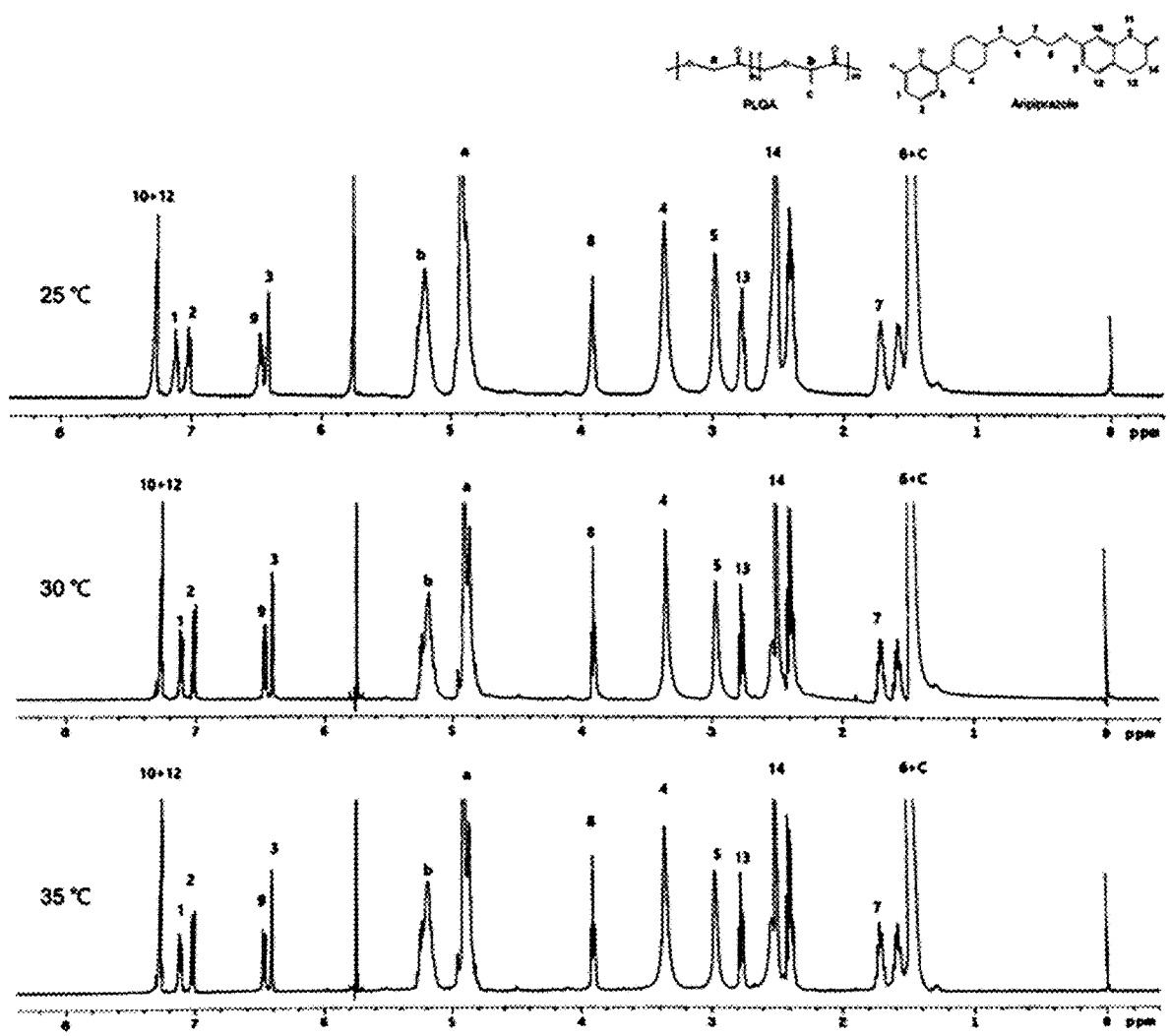
FIG. 8 is a set of 1H-NMR analysis results of a microcapsule containing aripiprazole prepared by varying the temperature of a solution according to an embodiment of the present invention.

As a result of measuring the microcapsules prepared by varying solvents of the drug dispersion solutions in Examples 4-1 to 4-4 using 1H-NMR, it could be confirmed that respective microcapsules in which aripiprazole was encapsulated in polylactide-co-glycolide (PLGA) were prepared (FIG. 8).

Figure 9:
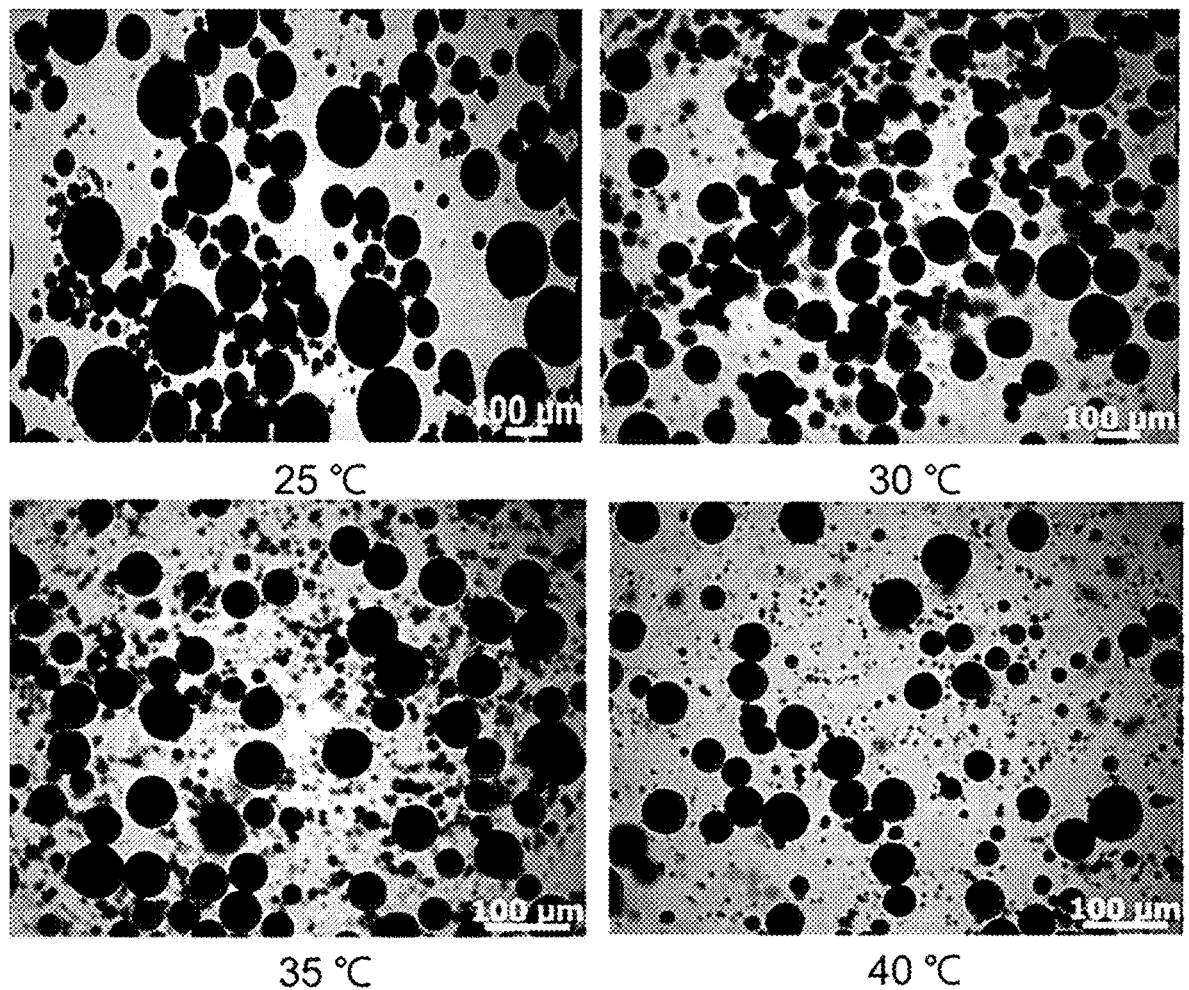
FIG. 9 is a set of particle size optical microscope images of a microcapsule containing aripiprazole prepared by varying the temperature of a solution.

In addition, after 10 mg of each prepared microcapsules was suspended in distilled water, the particle sizes of the microcapsules were measured and the optical microscope images were confirmed using a Zeta potential & Particle size analyzer. In consideration of the error range, the particle size values measured repeatedly three times are shown in the following Table 7, and the optical microscope images are shown in FIG. 9.

TABLE 7

|  | 25° C. | 30° C. | 35° C. | 40° C. |
|---|---|---|---|---|
| Particle size (μm) | 80.67 ± 3.97 | 65.66 ± 4.69 | 57.31 ± 11.93 | 30.68 ± 1.77 |

In order to observe the preparation efficiency of the microcapsule according to the preparation method varying the temperature of the drug dispersion solution, the yield and encapsulation efficiency of the microcapsule in which aripiprazole was encapsulated were measured.

Specifically, the yields of the microcapsules prepared in Examples 4-1 to 4-4 were compared with the amounts added by measuring the entire weight of the microcapsules, and the encapsulation efficiency of the microcapsule was calculated using [encapsulation efficiency=(drug content of the resulting aripiprazole capsule/drug content of the theoretical aripiprazole capsule)×100].

The 'drug content of the resulting aripiprazole capsule' was measured by comparing the PLGA area value peak (δ=4.8 to 4 ppm, 5 to 5.4 ppm) with the anhydrous aripiprazole area value peak (δ=7.1 ppm) from a result of measurement using 1H-NMR after dissolving a microcapsule to which a reference material was added in DMSO. As another method, the 'drug content of the resulting aripiprazole capsule' was measured using HPLC (Agilent-1200, USA) after 10 mg of the microcapsule was taken, dissolved in a mobile phase, and filtered. As the measurement conditions of HPLC, a C18 column (5 μm, 4.6×250 mm I.D.) (Thermo Scientific) was used, detection was performed at a wavelength of 254 nm, the mobile phase was aqueous anhydrous sodium sulfate solution:acetonitrile:methanol:acetic acid=56:33:11:1 (v/v), the flow rate was 1 ml/min, the injection volume was 100 μl, and the drug content was measured at 25° C.

The yield and encapsulation efficiency of the microcapsule and the amount of the drug in 10 mg of the capsule are shown in the following Table 8.

TABLE 8

|  | Yield (%) | Encapsulation efficiency (%) | Amount (mg) of drug per 10 mg of capsule |
|---|---|---|---|
| 25° C. | 88 | 90.0 | 3.6 |
| 30° C. | 73 | 87.5 | 3.5 |
| 35° C. | 76 | 90.0 | 3.6 |
| 40° C. | 71 | 92.5 | 3.7 |

As a result of analyzing characteristics of the microcapsules prepared in Examples 4-1 to 4-4, it could be confirmed that the yield of the microcapsule prepared at 25° C., the encapsulation efficiency of the microcapsule prepared at 40° C. was the highest, and there was no significant difference in the content of the drug in the capsule according to the temperature condition.

Example 5. Preparation of Microcapsule Encapsulating Donepezil Base 5-1. Preparation of Microcapsule Using Methylene Chloride (MC) and Ethyl Acetate (EA) as Solvent A uniform drug dispersion solution was prepared by dissolving polylactide-co-glycolide (PLGA) having a molecular weight of 33,000 g/mol in ethyl acetate (EA) so as to have a concentration of 3 wt % and dissolving 2 wt % of donepezil in methylene chloride (MC). After the solution was put into a syringe, the solution was flowed through a single axis ultrasonic sprayer at a flow rate of 4 ml/min at room temperature. A microcapsule was formed by preparing 250 ml of an aqueous polyvinyl alcohol (PVA) solution, which is a 0.5 wt % aqueous solution, and spraying the drug dispersion solution at a vibration frequency of 60 Hz to disperse the drug dispersion solution in the aqueous polyvinyl alcohol solution. After the aqueous polyvinyl alcohol solution was stirred at 700 rpm at room temperature for 2 hours and stabilized, the resulting microcapsule was put into distilled water, washed four to five times, and freeze-dried, thereby obtaining a microcapsule in which donepezile was encapsulated.

5-2. Preparation of Microcapsule Using Methylene Chloride (MC) as Solvent

A microcapsule in which donepezil was encapsulated was prepared in the same manner as in Example 5-1, except that as the solvent dissolving PLGA in Example 5-1, methylene chloride (MC) was used instead of ethyl acetate (EA).

5-3. Preparation of Microcapsule Using Chloroform and Ethyl Acetate (EA) as Solvent A uniform drug dispersion solution was prepared by dissolving polylactide-co-glycolide (PLGA) having a molecular weight of 33,000 g/mol in ethyl acetate (EA) so as to have a concentration of 3 wt % and dissolving 2 wt % of donepezil in chloroform. After the solution was put into a syringe, the solution was flowed through a single axis ultrasonic sprayer at a flow rate of 4 ml/min at room temperature. A microcapsule was formed by preparing 250 ml of an aqueous polyvinyl alcohol (PVA) solution, which is a 0.5 wt % aqueous solution, and spraying the drug dispersion solution at a vibration frequency of 60 Hz to disperse the drug dispersion solution in the aqueous polyvinyl alcohol solution. After the aqueous polyvinyl alcohol solution was stirred at 700 rpm at room temperature for 2 hours and stabilized, the resulting microcapsule was put into distilled water, washed four to five times, and freeze-dried, thereby obtaining a microcapsule in which donepezil was encapsulated.

5-4. Preparation of Microcapsule Using Chloroform as Solvent

A microcapsule in which donepezil was encapsulated was prepared in the same manner as in Example 5-3, except that as the solvent dissolving PLGA in Example 5-3, chloroform was used instead of ethyl acetate (EA).

The solvents used in Examples 5-1 to 5-4 are shown in the following Table 9.

TABLE 9

| | PLGA | Donepezil base |
|---|---|---|
| Example 5-1 | Ethyl acetate (EA) | Methylene chloride (MC) |
| Example 5-2 | Methylene chloride (MC) | Methylene chloride (MC) |
| Example 5-3 | Ethyl acetate (EA) | Chloroform |
| Example 5-4 | Chloroform | Chloroform |

5-5. Analysis of Characteristics of Microcapsule

Figure 10:
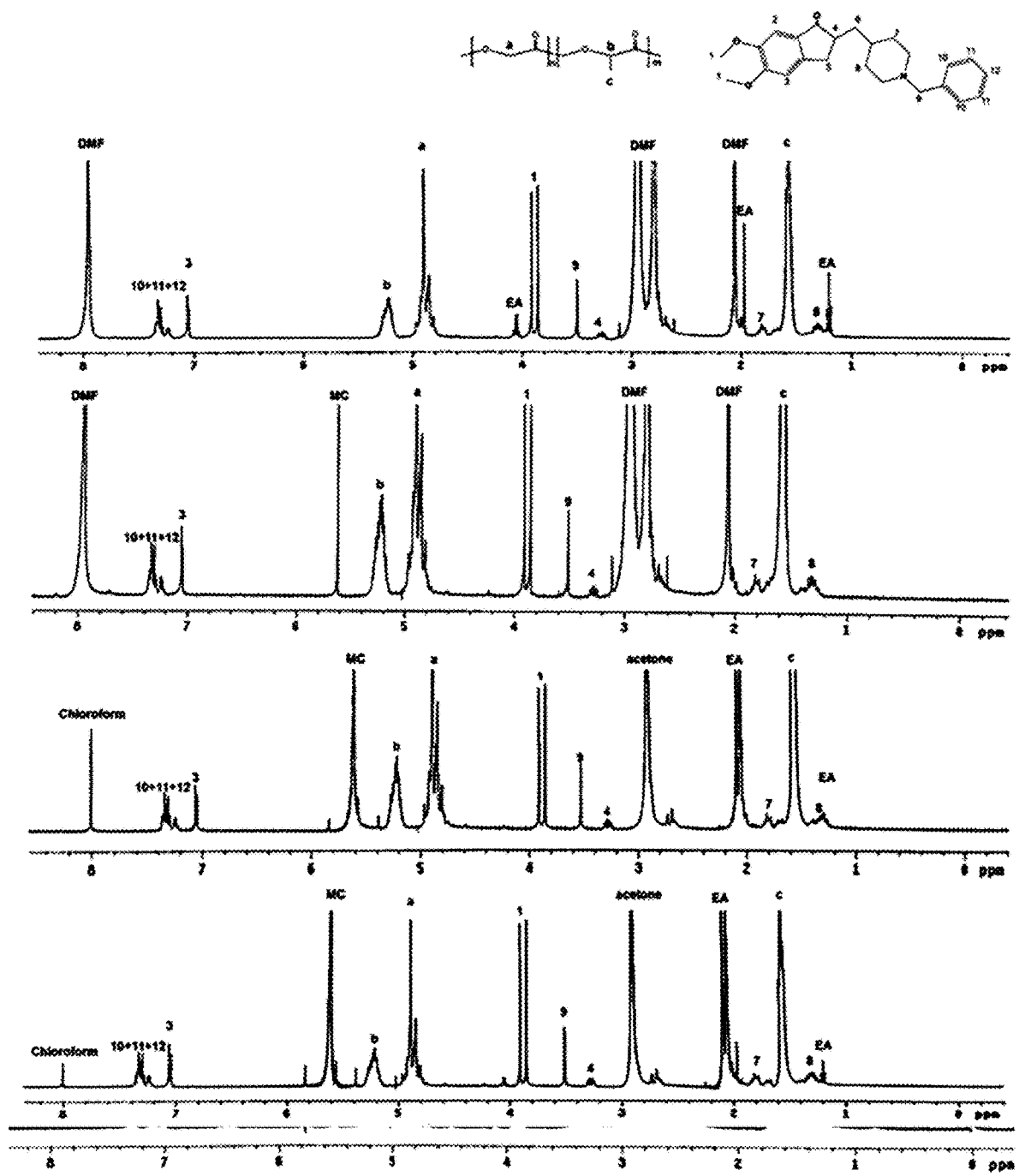
FIG. 10 is a set of 1H-NMR analysis results of a microcapsule containing donepezil prepared by varying solvents of a solution according to an embodiment of the present invention.

As a result of measuring the microcapsules prepared by varying solvents of the drug dispersion solutions in Examples 5-1 to 5-4 using 1H-NMR, it could be confirmed that respective microcapsules in which donepezil was encapsulated in polylactide-co-glycolide (PLGA) were prepared (FIG. 10).

Figure 11:
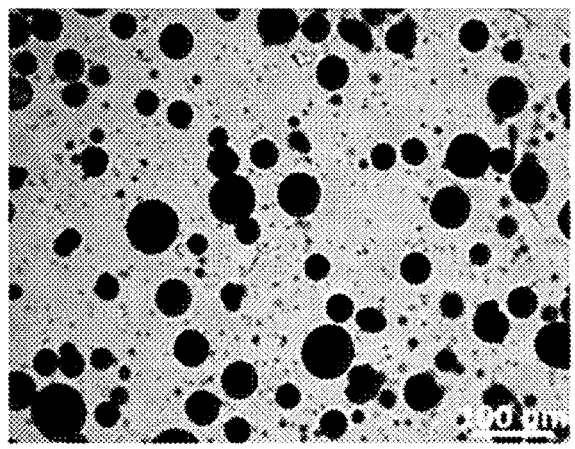
FIG. 11 is a set of optical microscope images of a microcapsule containing donepezil prepared by varying solvents of a solution.
Figure 11:
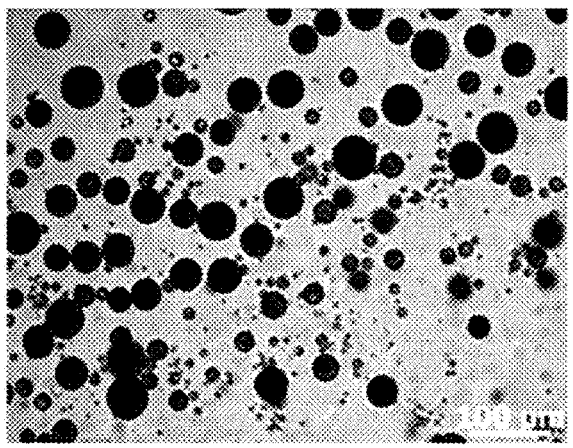
Figure 11:
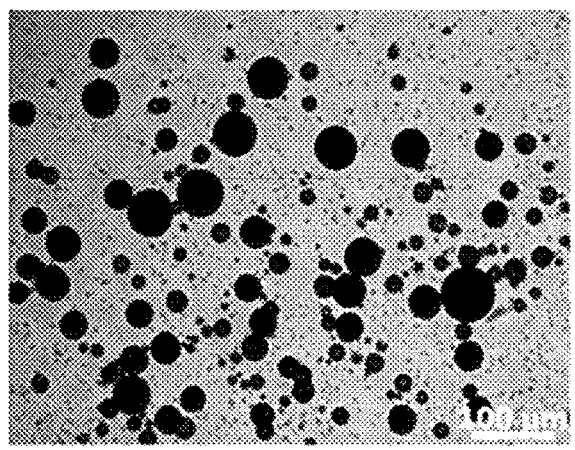
Figure 11:
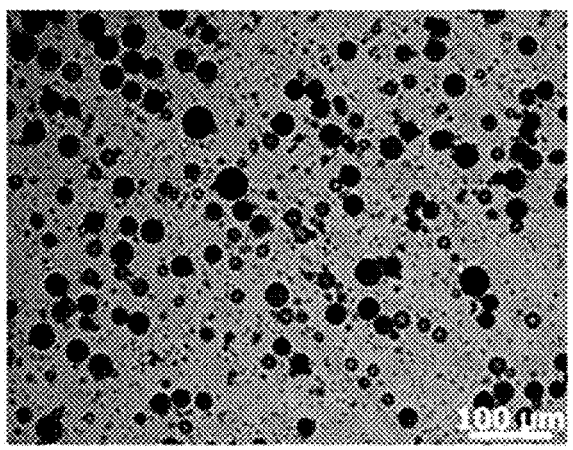

Further, the optical microscope images of the prepared microcapsule were confirmed. The optical microscope images are shown in FIG. 11.

In order to evaluate the preparation efficiency of the microcapsule according to the preparation method varying the solvents of the drug dispersion solution, the yield and drug content of the microcapsule in which donepezil was encapsulated were measured.

Specifically, the yields of the microcapsules prepared in Examples 5-1 to 5-4 were compared with the amounts added by measuring the entire weight of the microcapsules, and the encapsulation efficiency of the microcapsule was calculated using [encapsulation efficiency=(drug content of the resulting donepezil capsule/drug content of the theoretical donepezil capsule)×100].

The 'drug content of the resulting donepezil capsule' was measured by comparing the PLGA area value peak ($\delta$=4.8 to 4 ppm, 5 to 5.4 ppm) with the donepezil area value peak ($\delta$=7.1 ppm) from a result of measurement using 1H-NMR after dissolving a microcapsule to which a reference material was added in acetone. The 'drug content of the resulting donepezil capsule' was measured by the HPLC shown in Example 1-4 as another method.

The yield and encapsulation efficiency of the microcapsule and the amount of the drug in 10 mg of the capsule are shown in the following Table 10.

TABLE 10

| | Yield (%) | Encapsulation efficiency (%) | Amount (mg) of drug per 10 mg of capsule |
|---|---|---|---|
| Example 5-1 | 60.8 | 88.0 | 2.2 |
| Example 5-2 | 86.5 | 60.0 | 1.5 |
| Example 5-3 | 70.2 | 16.0 | 0.4 |
| Example 5-4 | 53.6 | 52.0 | 1.3 |

As a result of analyzing characteristics of the microcapsules prepared in Examples 5-1 to 5-4, the encapsulation efficiency and drug content of the microcapsule prepared by using ethyl acetate (EA) and dissolving the drug in methylene chloride (MC) during the preparation of PLGA were the highest.

Example 6. Preparation of Crosslinked Small Intestinal Submucosa Hydrogel

After a reaction was carried out by introducing 1 wt % of a small intestinal submucosa powder, 0.1 wt % of pepsin, and 3 wt % of acetic acid based on the total weight of the entire solution, and stirring the resulting mixture for 48 hours, a small intestinal submucosa solution was prepared by introducing a 1 N sodium hydroxide solution so as to have a pH of 7.4, and then freeze-dried for 3 to 4 days to make the solution in the form of a powder.

After the prepared small intestinal submucosa freeze-dried powder was dissolved in a phosphate buffer solution (PBS, pH 7.4) at a concentration of 20 wt %, a reaction was carried out by introducing methyltetrazine-PEG4-NHS-ester (TET) and trans-cyclooctene-PEG4-NHS-ester (CO) thereto so as to have a molar ratio of 1:500 and stirring the resulting mixture for 24 hours. Thereafter, the mixture was dialyzed and freeze-dried for 48 hours, and then dissolved in a phosphate buffer solution (PBS, pH 7.4), thereby preparing a crosslinked small intestinal submucosa hydrogel.

Example 7. Preparation of Crosslinked Hyaluronic Acid Gel

A hyaluronic acid solution was prepared by introducing 1 wt % of hyaluronic acid into tertiary distilled water and stirring the resulting mixture at room temperature for 12 hours. After 97.6 mg of 100 mM 2-(N-morpholino)ethane-sulfonic acid and 3.5 g of 2.5 M 4-(4,6-dimethoxy-1,3,5-triazine-2yl)-4-methylmorpholinium chloride were introduced into the hyaluronic acid solution, a reaction was carried out by introducing methyltetrazine-PEG4-NHS-amine (TET) and trans-cyclooctene-PEG4-NHS-amine (CO) thereto so as to have a molar ratio of 1:500 and stirring the resulting mixture for 72 hours. Thereafter, the mixture was dialyzed and freeze-dried for 72 hours, and then dissolved in a phosphate buffer solution (PBS, pH 7.4), thereby preparing a crosslinked hyaluronic acid hydrogel.

Figure 12:
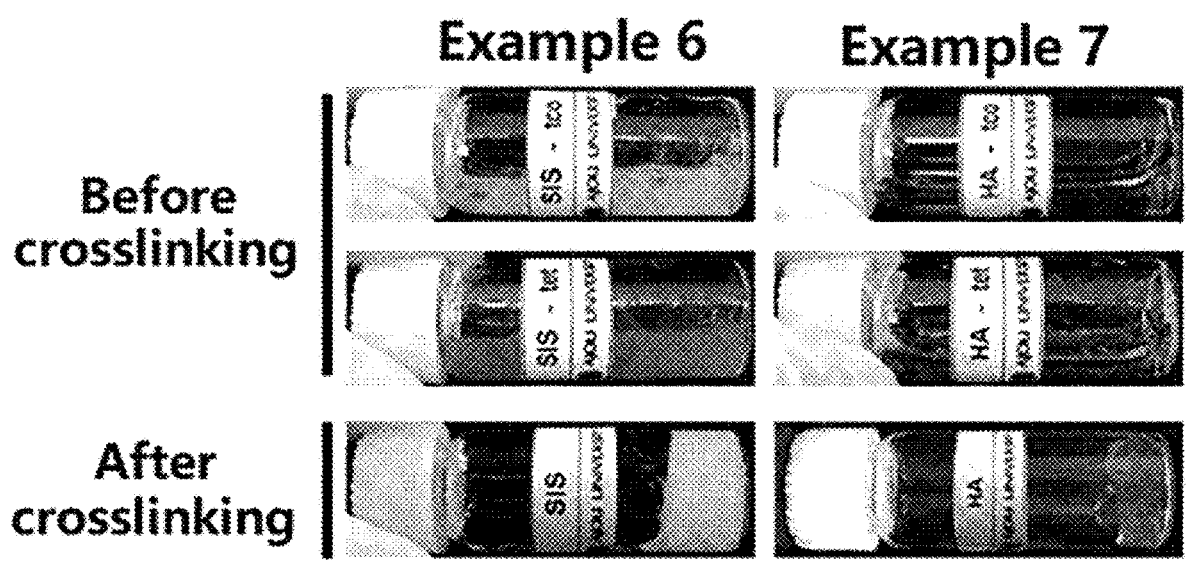
FIG. 12 is a set of images of a hydrogel prepared according to an embodiment of the present invention.

The shapes of the crosslinked hydrogels prepared in Examples 6 and 7 are shown in FIG. 12.

Example 8. Measurement of Released Amount of In Vitro Anhydrous Aripiprazole

Figure 13:
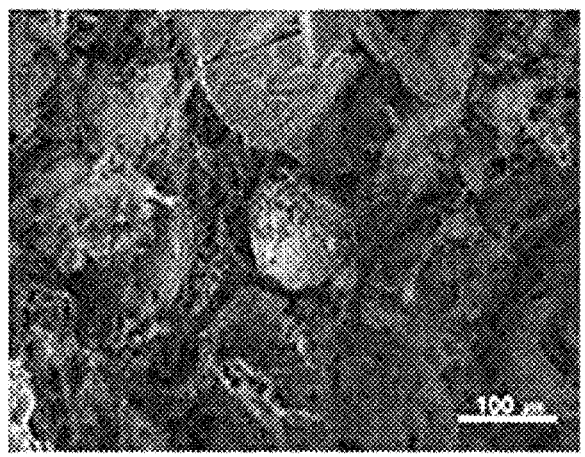
FIG. 13 is a set of SEM images of a microcapsule in a hydrogel.
Figure 13:
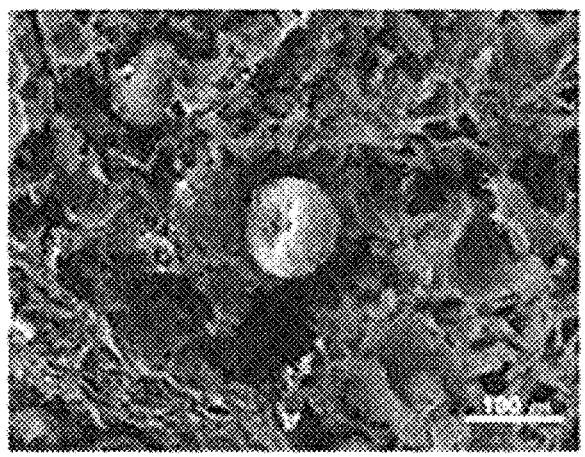

After 25 mg of each of the microcapsules prepared in Examples 1 and 2 was weighed and dispersed in 1 ml of each of the crosslinked hydrogels prepared in Examples 6 and 7, an anhydrous aripiprazole drug delivery formulation was prepared by putting the dispersion into a 5-ml vial. Through SEM images of the drug delivery formulation, the microcapsule dispersed in the hydrogel could be confirmed (FIG. 13).

Figure 14:
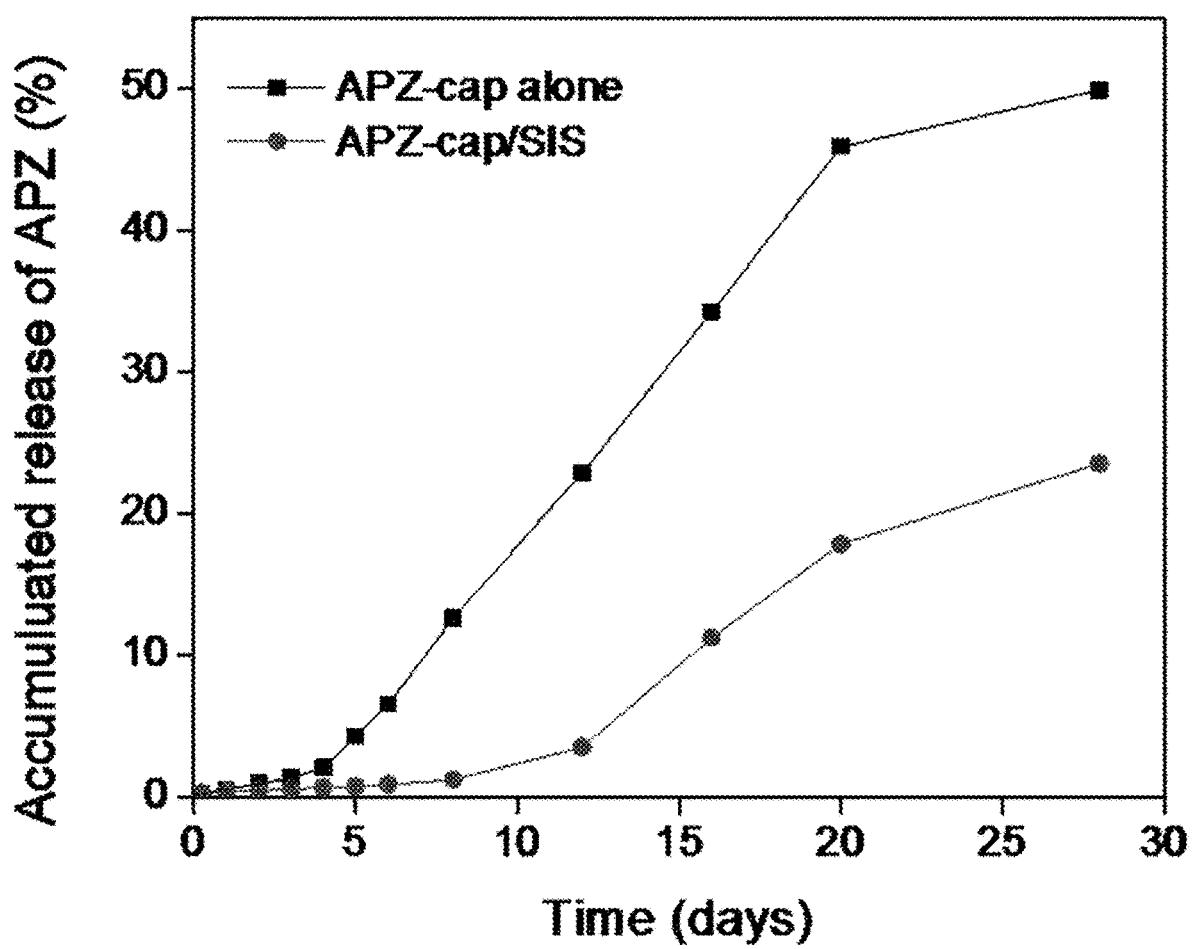
FIG. 14 is a drug release result of anhydrous aripiprazole.

After 4 ml of PBS was added to the vial of the anhydrous aripiprazole drug delivery formulation using the small intestinal submucosa hydrogel, 0.5 ml of PBS was taken under the conditions of 37° C. and 100 rpm at each predetermined interval, and sampling was performed at each time while adding an equal amount of new PBS thereto. The microcapsule (APZ-cap alone) in Example 1-1 was used as a control, the amount of anhydrous aripiprazole released was measured from each microcapsule using HPLC, and the measurement conditions were employed in the same manner as in the conditions under which the encapsulation efficiencies of Examples 1 to 5 were measured. The results of measuring the released amount of in vitro anhydrous aripiprazole are illustrated in FIG. 14.

As a result, the microcapsule single formulation exhibited a tendency of the drug to be released in excess within a short time, but in the case of the microcapsule dispersed in the small intestinal submucosa hydrogel, it could be confirmed that the drug was released slowly for a long period of time.

Example 9. Measurement of Released Amount of In Vitro Aripiprazole

After 25 mg of each of the microcapsules prepared in Examples 3 and 4 was weighed and dispersed in 1 ml of each of the crosslinked hydrogels prepared in Examples 6 and 7, an aripiprazole drug delivery formulation was prepared by putting the dispersion into a 5-ml vial.

Figure 15:
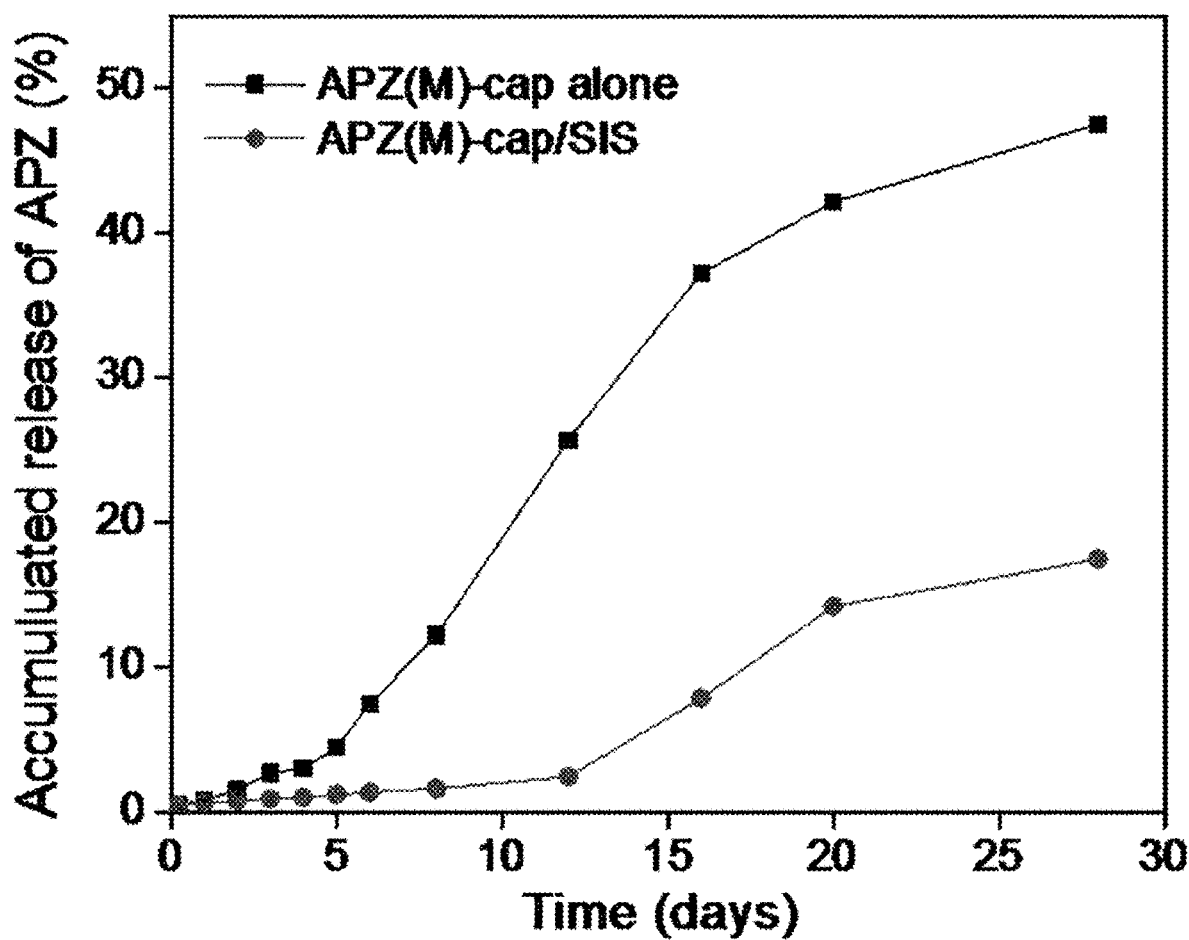
FIG. 15 is a drug release result of aripiprazole.

After 4 ml of PBS was added to the vial of the aripiprazole drug delivery formulation using the small intestinal submucosa hydrogel, 0.5 ml of PBS was taken under the conditions of 37° C. and 100 rpm at each predetermined interval, and sampling was performed at each time while adding an equal amount of new PBS thereto. The microcapsule (APZ-cap alone) in Example 3-1 was used as a control, the amount of released aripiprazole was measured from each microcapsule using HPLC, and the measurement conditions were employed in the same manner as in the conditions under which the encapsulation efficiencies of Examples 1 to 5 were measured. The results of measuring the released amount of in vitro aripiprazole are illustrated in FIG. 15.

As a result, it could be confirmed that in the case of the microcapsule dispersed in the small intestinal submucosa hydrogel, the drug was released slowly for a long period of time as compared to the microcapsule single formulation.

Example 10. Preparation of Granular Single Group Injectable Formulation

Each of the microcapsules containing aripiprazole prepared in Examples 1 to 4, 5 wt % of D-mannitol, 2 wt % of carboxymethylcellulose (CMC), and 0.1% Tween 80 were uniformly dispersed in distilled water, put into a 1-ml syringe, and prepared as an injectable formulation. Immediately after the preparation, a gel was formed by injecting the formulation into the hypodermis of a model mouse.

Figure 16:
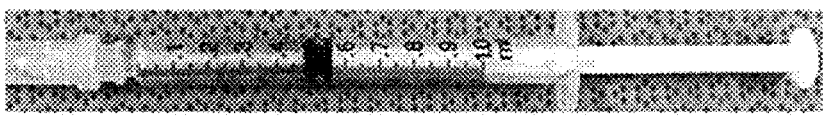
FIG. 16 is a set of images of an injectable formulation of a hydrogel containing a microcapsule prepared according to an embodiment of the present invention.
Figure 16:
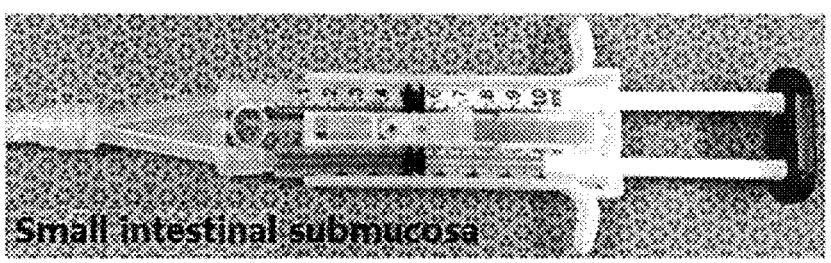
Figure 17:
FIG. 17 is a set of images in which a hydrogel injectable formulation of an embodiment of the present invention is injected into the hypodermis of a mouse.
Figure 17:
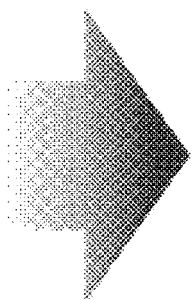
Figure 17:
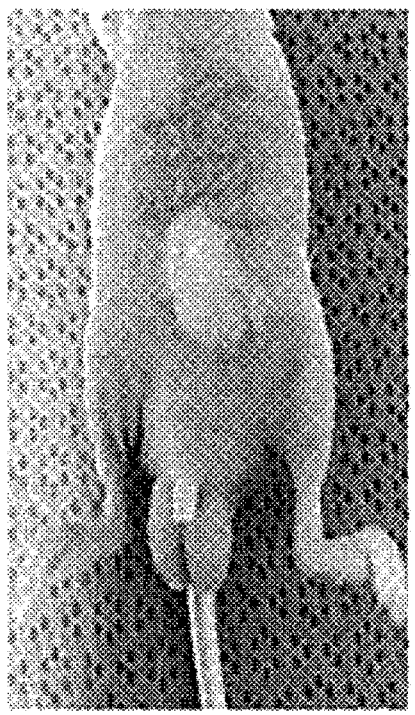

Example 11. Preparation of Injectable Formulation in which Microcapsule is Dispersed in Hydrogel After each of the microcapsules containing aripiprazole prepared in Examples 1 to 4 was uniformly dispersed in 1 ml of each of the hydrogels prepared in Examples 6 and 7, the dispersion was put into a 1-ml syringe and prepared as an injectable formulation (FIG. 16). Immediately after the preparation, a gel was formed by injecting the formulation into the hypodermis of a model mouse (FIG. 17).

It could be confirmed that when the injectable formulations prepared in Examples 10 and 11 were injected into the hypodermis of a model mouse, a gel in which the drug-containing microcapsule was dispersed was formed in the hypodermis, and it was confirmed that the drug was released slowly from the injected gel for 4 weeks or more, thereby exhibiting a sustained therapeutic effect for a long period of time.

The invention claimed is:

1. A method for treating a mental illness or a central nervous system disorder in a subject in need thereof, the method comprising:
    administering to the subject a sustained-release drug delivery formulation,
    said sustained-release drug delivery formulation comprising
        a hydrogel selected from a small intestinal submucosa hydrogel or hyaluronic acid hydrogel, in which a tetrazine-containing compound and a cyclooctene-containing compound are crosslinked to each other, wherein molar ratio of the hydrogel and a sum of the tetrazine-containing compound and the cyclooctene-containing compound is 1:400 to 1:600; and
        a microcapsule formed of a biodegradable polymer and encapsulating a psychopharmaceutical agent, an antidepressant, or a drug for treating a central nervous system disease, dissolved in methylene chloride;
    wherein the hydrogel comprises a biodegradable polymer at a concentration of 1 to 30 wt % based on total weight of the hydrogel,
    wherein the tetrazine-containing compound is one or more selected from the group consisting of methyltetrazine-amine, methyltetrazine-PEG4-amine, methyltetrazine-propylamine, tetrazine-PEG5-NHS ester, methyltetrazine-PEG4-NHS ester, methyltetrazine-PEG4-NHS amine, methyltetrazine-silfo-NHS ester, methyltetrazine-PEG4-acid, methyltetrazine-PEG12-NHS ester, methyltetrazine-NHS ester, methyltetrazine-acid, and tetrazine-acid,
    wherein the cyclooctene-containing compound is one or more selected from the group consisting of trans-cyclooctene-amine, trans-cyclooctene-NHS ester, trans-cyclooctene-NHS amine, trans cyclooctene-PEG-NHS ester, and trans cyclooctene-PEG4-acid, and
    wherein the microcapsule is dispersed in the hydrogel.

2. The method of claim 1, wherein the biodegradable polymer is selected from the group consisting of polylactide-co-glycolide (PLGA), polyethylene glycol (PEG), caprolactone (CL), glycolide (GA), lactide (LA), and a combination thereof.

3. The method of claim 1, wherein the biodegradable polymer has a molecular weight of 10,000 to 200,000 g/mol.

4. The method of claim 1, wherein the microcapsule further comprises one or more additives selected from the group consisting of an antiseptic, a preservative, an excipient, and a combination thereof.

5. The method of claim 1, wherein the drug delivery formulation is an injectable formulation.

6. The method of claim 1, wherein the mental illness is one or more selected from the group consisting of schizophrenia, bipolar disorder, non-bipolar mania, Tourette syndrome, cyclothymic disorder, rapid cycling, ultradian cycling, personality disorder, attention disorder, delusional disorder, psychotic disorder, psychotic disorder related to Parkinson's disease, anxiety disorder, panic disorder, post-traumatic stress disorder, impulse control disorder, phobic disorder, dissociative states, and depression.

7. The method of claim 1, wherein the central nervous system disorder is one or more selected from the group consisting of brain tumors, cerebral infarction, hypertensive intracerebral hemorrhage, cerebral contusion, cerebral arteriovenous malformation, brain abscesses, encephalitis, hydrocephalus, epilepsy, cerebral concussions, cerebral palsy, dementia, spinal cord tumors, spinal arteriovenous malformation, and spinal cord infarction.

* * * * *